United States Patent [19]
Kun et al.

[11] Patent Number: 5,877,185
[45] Date of Patent: Mar. 2, 1999

[54] SYNERGISTIC COMPOSITIONS USEFUL AS ANTI-TUMOR AGENTS

[75] Inventors: Ernest Kun, Mill Valley; Jerome Mendeleyev, Tiburon; Eva Kirsten, Daly City, all of Calif.

[73] Assignee: Octamer, Inc., Mill Valley, Calif.

[21] Appl. No.: 377,584

[22] Filed: Jan. 13, 1995

Related U.S. Application Data

[63] Continuation-in-part of Ser. No. 76,313, Jun. 11, 1993, Pat. No. 5,464,871, which is a continuation-in-part of Ser. No. 60,409, May 12, 1993, abandoned, and a continuation-in-part of Ser. No. 87,566, Jul. 2, 1993, which is a continuation-in-part of Ser. No. 965,541, Nov. 2, 1992, Pat. No. 5,516, 941, which is a continuation-in-part of Ser. No. 893,429, Jun. 4, 1992, abandoned, which is a continuation-in-part of Ser. No. 780,809, Oct. 22, 1991, abandoned.

[51] Int. Cl.$^6$ .......................... A61K 31/47; A61K 31/35; C07D 217/24; C07D 311/08
[52] U.S. Cl. .......................... 514/309; 514/456; 546/141; 549/287
[58] Field of Search .................................. 514/309, 456; 546/141; 549/287

[56] References Cited

U.S. PATENT DOCUMENTS

| | | | |
|---|---|---|---|
| 3,974,289 | 8/1976 | Buckle et al. | 514/457 |
| 4,012,407 | 3/1977 | Doyle et al. | 558/426 |
| 4,032,544 | 6/1977 | Doyle et al. | 549/280 |
| 4,737,517 | 4/1988 | della Valle et al. | 514/457 |
| 4,845,121 | 7/1989 | Witiak et al. | 514/455 |

FOREIGN PATENT DOCUMENTS

| | | |
|---|---|---|
| 371 560 A3 | 6/1990 | European Pat. Off. . |
| 2036017 | 6/1980 | United Kingdom . |
| 2244646 | 12/1991 | United Kingdom . |
| WO 89/07441 | 8/1989 | WIPO . |
| WO 89/07939 | 9/1989 | WIPO . |
| WO 92/06687 | 4/1992 | WIPO . |
| WO 93/07868 | 4/1993 | WIPO . |

OTHER PUBLICATIONS

Goldstein, H., "Sur l'acide 5–nitro–2–ido–benzoique", *Helv. Chim. Acta*, 13:310–314 (1930).

Aldovini and Young. "Mutations of RNA and Protein Sequences Involved in Human Imunodeficiency Virus Type 1 Packaging Result in Production of Noninfectious Virus". *Journal of Virology* 64:1920–1926 (1990).

Buki, K.G. et al. "Inhibitory Binding of Adenosine Diphosphoribosyl Transferase to the DNA primer Site of Reverse Transciptase Templates". *Biochemical and Biophysical Research Communications*. 180:496–503 (1991).

Buki, K.G. et al. "Destabilization of $Zn^{2+}$Coordination in ADP–ribose transferase (Polymerizing) by 6–nitroso–1, 2–benzopyrone coincidental with inactivation of the polymerase but not the DNA binding function". *Federation of European Biochemical Societies* 290:181–185 (1991).

Chuang, A.J. et al. "Chemotherapeutic activity of 4–iodo–3–nitrobenzamde and 5–iodo–6–amino–1,2–benzopyrone on Simian Immunodeficiency Virus (SIV) in cultures of CEM x 174 cells". (submitted, 1994).

Cole, G.A. et al. "Inhibition of HIV–1 lllb Replication in AA–2 and MT–2 Cells in Culture By Two Ligands of Poly (ADP–RIBOSE) Polymerase: 6–Amino–1,2–Benzopyrone and 5–Iodo–6–Amino–1,2–Benzopyrone". *Biochemical and Biophysical Research Communications* 180:504–514 (1991).

Ehlhardt, W.J. et al. "Nitrosoimidazoles: Highly Bactericidal Analogues of 5–Nitroimidazole Drugs". *J. Med. Chem.* 31:323–329 (1988).

Furlini, G. et al. "Increased Poly(ADP–PROSE) Polymerase Activity in Cells Infected by Human Immunodeficiency Virus Type–1". *Microbiological* 14:141–148 (1991).

Gorelick, R.J. et al. "Point mutants and Moloney murine leukemia virus that fail to package viral RNA: Evidence for specific RNA recognition by a zinc finger–like protein sequence". *Proc. Natl. Acad. Sci. USA* 85:8420–8424 (1988).

Gorelick, R.J. et al. "Ioninfectious Human Immunodeficiency Virs Type 1 Mutants Deficient in Genomic RNA". *Virology* 64:3207–3211 (1990).

Gradwohl, G. et al. "The second zinc–finger domain of poly (ADP–ribose) polymerase determines specificity for single–stranded breaks in DNA". *Proc. Natl. Acad. Sci. USA* 87:2990–2994 (1990).

Henderson, L.E. et al. "Primary Structure of the Low Molecular Weight Nucleic Acid–binding Proteins of Murine Leukemia Viruses". *Biological Chemistry* 256:8400–8406 (1981).

Kirsten, E. et al. "Cellular Reglation of ADP–Ribosylation of Proteins". *Experimental Cell Research* 194:1–8 (1991).

Kovacic, P. et al. "Reduction Potentials in Relation to Physilogical Activities of Benzenoid and Heterocyclic Nitroso Compounds: Comparison with the Nitro Precursors". *Bioorganic Chemistry* 18:265–275 (1990).

Krasil'nikov, I.I. et al. "Inhibitors of ADP–Ribosylation as Antiviral Drugs: An Experimental Study on the Model of HIV Infection". *Voprosy Virusologii* 3:216–218 (1991).

(List continued on next page.)

*Primary Examiner*—C. Warren Ivy
*Assistant Examiner*—D. Margaret M. Mach
*Attorney, Agent, or Firm*—Albert P. Halluin; Howrey & Simon

[57] ABSTRACT

The subject invention provides for novel synergistic compositions useful for inactivating viruses or inducing apoptosis in tumor cells and for treating cancer or retroviral infections. Generally, the compositions comprise one or a plurality of ligands that oxidatively attack a zinc finger of pADPRT in combination with one or a plurality of agents selected from the group consisting of: agents that decrease cellular levels of glutathione and ligands that non-covalently bind to the nicotinamide site of pADPRT but do not effect zinc ejection from a zinc finger of pADPRT.

6 Claims, 9 Drawing Sheets

OTHER PUBLICATIONS

Kun, E. et al. "Reversion of malignant phenotype and induction of apoptosis by ligands of poly (ADP–ribose) polymerase". (submitted, 1994).

Lever, A. et al. "Identification of a Sequence Required for Efficient Packaging of Human Immunodeficiency Virus Type 1 RNA into Virus". *Virology* 63:4085–4087 (1989).

Liebmann, J. et al. "Glutathione Depletion by L–Buthionine Sulfoximine Antagonizes Taol Cytotoxicity". *Cancer Research* 53:2066–2070 (1993).

McClelland, R.A. et al. "Products of the Reductions of 2–Nitroimidazoles". *J. Am. Chem. Soc.* 109:4308–4314 (1987).

Mendeleyev, J. et al. "Potential Chemotherapeutic Activity of 4–Iodo–3–Nitrobenzamide. Metabolic Reduction to the 3–Nitroso Deriative and Induction of Cell Death in Tumor Cells in Culture ". (submitted, 1994).

Meric and Goff. "Characterization of Moloney Murine Leukemia Virus Mutants with Single–Amino–Acid Substitutions in the Cys–His Box of the Nucleocapsid". *Virology* 63:1558–1568 (1989).

Mulcahy, R.T. et al. "Cytotoxiciy and Glutathione Depletion by 1–Methyl–2–Nitrosoimidazole in Human Colon Cancer Cells". *Biochemical Pharmacology* 38:1667–1671 (1989).

Noss, M.B. et al. "Preparation, Toxicity and Mutagenicity of 1–Methyl–2–Nitrosoimidazole". *Biochemical Pharmacology* 37:2585–2593 (1988).

Noss, M.B. et al. "1–Methyl–2–Nitrosoimidazole: Cytotoxic and Glutathione Depleting Capabilities". *Int. J. Radiation Oncology Biol. Phys.* 16:1015–1019 (1989).

Polhuijs, M. et al. "Relationship between glutathione content in liver and glutathione conjugation rate in the rat in vivo". *Biochem J.* 285:410–404 (1992).

Irne–Rasa and Koubek. "o–Nitrosobenzamide. A Possible Intermediate in the von Richter Reaction". *J. Org. Chem.* 28:3240–3241 (1963).

Rice, W.G. et al. "Inhibition on HIV–1 infectivity by zinc–ejecting aromatic C–nitroso compounds". *Nature* 361:473–475 (1993).

Rice, W.G. et al. "Induction of endonuclease–mediaed apoptosis in tumor cells by C–nitroso–substituted ligands of poly (ADP–ribose) polymerase". *Proc. Natl. Acad. Sci. USA* 89:7703–7707 (1992).

South, T.L. et al. "Cd NMR Studies of a 1:1 Cd Adduct with an 18–Residue Finger Peptide from HIV–1 Nucleic Acid Binding Protein, p7". *J. Am. chem. Soc.* 111:395–396 (1989).

South, T.L. et al. "Zinc fingers and molecular recognition. Structure and nucleic acid binding studies of an HIV zinc finger–like domain". *Biochem. Pharm.* 40:123–129 (1990).

Summers, M.F. et al. "High–Resolution Strcture of an HIV Fingerlike Domain via a New NMR–Based Distance Geometry Approach". *Biochemistry* 29:329–340 (1990).

Terradez, P. et al. "Depletion of tumour glutathione in vivo by buthionine sulphoximine: modulation by the rate of cellular proliferation and inhibition of cancer growth". *Biochem. J.* 292:477–483 (1993).

Varghese and Whitmore. "Modification of Guanine Dervatives by Reduced 2–Nitroimidazoles". *Cancer Research* 43:78–82 (1983).

Yamagoe, S. et al. "Poly (ADP–Ribose) Polymerase Inhibitors Suppress UV–Induced Human Immunodeficiency Virus Type 1 Gene Expression at the Pasttranscriptional Level". *Molecular and Cellular Biology* 11:3522–3527 (1991).

Yao, K. et al. "Variable Baseline y–Glutamylcyseine Synthetase Messenger RNA Expression in Peripheral Mononuclear Cells of Cancer Patients, and Its Induction by Buthionine Sulfoximine Treatment". *Cancer Research* 53:3662–3666 (1993).

FIG. 1
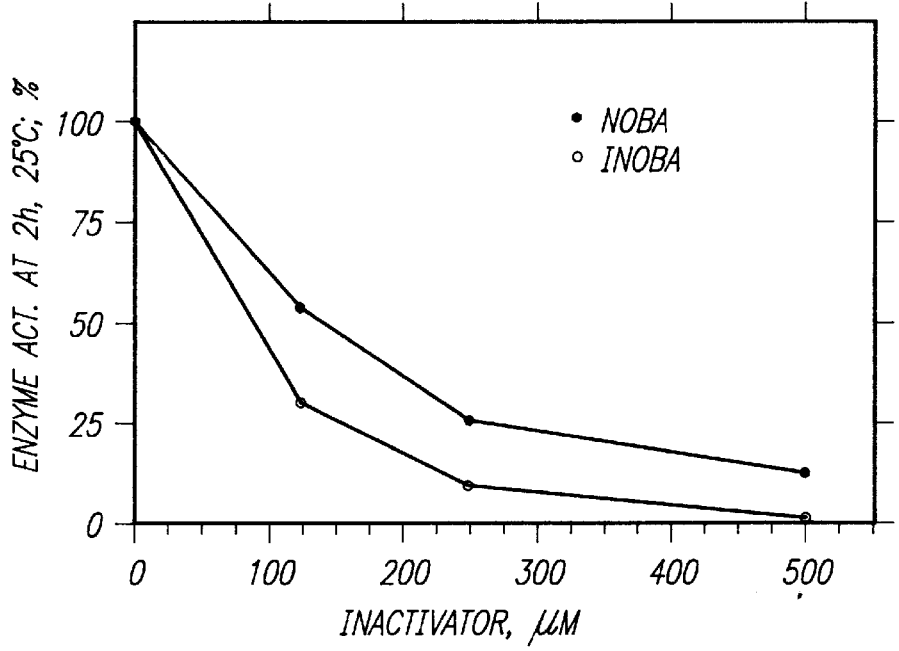
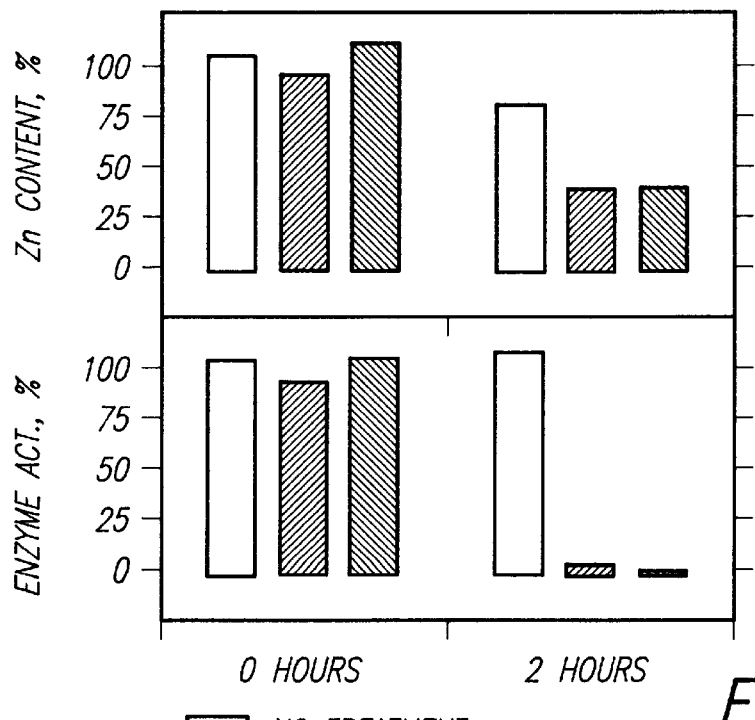
FIG. 2A

SYNERGISTIC COMPOSITIONS USEFUL AS ANTI-TUMOR AGENTS

CROSS REFERENCE

This is a continuation-in-part of U.S. application Ser. No. 08/076,313 filed Jun. 11, 1993 now U.S. Pat. No. 5,464,871, which is a continuation-in-part of co-pending U.S. application Ser. No. 08/060,409 filed May 12, 1993 now abandoned; and co-pending U.S. application Ser. No. 08/087,566 filed Jul. 2, 1993, which is a continuation-in-part of U.S. application Ser. No. 07/965,541 filed Nov. 2, 1992 now U.S. Pat. No. 5,516,941, which is a continuation-in-part of U.S. Ser. No. 07/893,429 filed Jun. 4, 1992 now abandoned, which is a continuation-in-part of U.S. Ser. No. 07/780,809 filed Oct. 22, 1991 now abandoned.

FIELD OF THE INVENTION

The present invention relates generally to the fields of retroviral and cancer therapeutic and inactivating agents and to their use in treating retroviral infections and cancer. More specifically, the present invention relates to novel synergistic compositions useful as potent, selective and safe anti-tumor or anti-retroviral agents. The synergistic compositions comprise one or a plurality of ligands that oxidatively attack a zinc finger of poly (ADP-ribose) polymerase ("pADPRT") in combination with one or a plurality of agents selected from the group consisting of: agents that decrease cellular levels of glutathione ("GSH decreasing agents") and ligands that bind non-covalently to the nicotinamide site of pADPRT but do not eject zinc from a zinc finger of pADPRT ("pADPRT-inhibitory ligands").

The invention also relates generally to methods for treating tumorigenic and retroviral diseases using said synergistic compositions.

BACKGROUND OF THE INVENTION

Cancer and viral infections are a serious threat to modern society. Malignant cancerous growths, due to their unique characteristics, pose serious challenges for modern medicine. These characteristics include: uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

Antineoplastic chemotherapy currently encompasses several groups of drugs including alkylating agents, purine antagonists and antitumor antibiotics. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of development of acute leukemia.

Purine, pyrimidine and folate antagonists are cell cycle and phase specific and, in order to promote an anti-tumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimidine antagonists, such as cytarabine, 5-fluorouracil or floxuridine inhibit DNA synthesis by inhibiting deoxycytidylate kinase and DNA polymerase.

Folate antagonists, e.g., methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and actinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions.

Thus, it would be extremely advantageous to provide safe and non-toxic chemotherapeutic compositions which would effectively inhibit cancer cell proliferation and suppress neoplastic growth. *The Merck Manual*, 1218–1225 (1987), 15th Ed. Novel synergistic compositions of this invention provide such treatment.

Similar to cancer, the high degree of infectiousness and fast reproduction cycle of viruses within host organisms make viruses a nuisance and a health hazard.

There is no simple treatment of viral diseases. Viruses are not susceptible to antibiotics. The only available treatment of viral diseases is chemotherapy utilizing viral replication inhibitors in host cells. *The Merck Manual*, 170, 14th Ed. (1982). Examples of these chemical agents are idoxuridine, acyclovir, ribavirin, vidarabine, gancyclovir, adenine arabinoside (ABA-A) and AZT. These, and other viral replication inhibitors, however, are cytotoxic, hepatotoxic, neurotoxic, nephrotoxic and teratogenic. *Virus Diseases*, 1–6, Crown Publishers, N.Y. (1978).

Human immunodeficiency virus (HIV) infections known as acquired immunodeficiency syndrome (AIDS), presently constitute a worldwide health hazard. HIV infections are almost always fatal due to a weakened immunoresistance, leading to opportunistic infections, malignancies and neurologic lesions.

There is no effective treatment for AIDS other than the treatment of the opportunistic infections, neoplasms and other complications. Available cytostatic (AZT) and antiviral (acyclovir) drugs are extremely toxic and cause severe adverse reactions. In addition, opioid drug addiction coincides with the emergence of AZT resistance, Chuang et al., *NIDA Res. Monograph: Problems of Drug Dependence* 14:419 (1993), thereby reducing the efficacy of AZT treatment for opioid-addicted AIDS patients.

Thus it would be highly desirable to have available an effective and yet nontoxic treatment of viral diseases, in particular, AIDS, and further for AZT-resistant patients or viral strains.

Cytomegalovirus (CMV), a dangerous co-infection of HIV, is a subgroup of highly infectious viruses having the propensity for remaining latent in man. CMVs are very common among the adult population and as many as 90% of adults have been exposed to and experienced CMV infections. CMVs are normally present in body liquids such as blood, lymph, saliva, urine, feces, milk, etc. CMV infections may cause abortion, stillbirth, postnatal death from hemorrhage, anemia, severe hepatic or CNS damage. Particularly dangerous are CMV infections afflicting AIDS patients, where CMV may cause pulmonary, gastrointestinal or renal complications. There is no specific therapy for CMVs. CMV is resistant to acyclovir, and to other known antiviral drugs.

Thus, it would be extremely advantageous to have available a drug which would effectively inhibit CMV infections.

Recently, a series of highly effective anti-tumor and anti-viral drugs were identified. These drugs include: substituted and unsubstituted 6-amino-1,2-benzopyrones which are the subject of copending U.S. patent application Ser. No. 08/237,969 filed on May 3, 1994, entitled "6-Amino-1,2-Benzopyrones Useful for Treatment of Viral Diseases;" 5-iodo-6-amino-1,2-benzopyrones and 5-iodo-6-nitroso-1,2-benzopyrones which are the subject of copending U.S. patent applications Ser. No. 07/600,593 filed on Oct. 19, 1990 entitled "Novel 5-Iodo-6-Amino-1,2-Benzopyrones and Their Metabolites Useful as Cytostatic and Antiviral Agents" and Ser. No. 08/021,989 filed on Feb. 24, 1993 entitled "Novel 5-Iodo-6-Amino-1,2-Benzopyrones and Their Metabolites Useful as Cytostatic Agents;" 3-nitrosobenzamides, 6-nitroso-1,2-benzopyrones and nitroso-1-(2H)-isoquinolinones which are the subject of copending U.S. patent applications Ser. Nos. 07/780,809, 07/893,429 and 07/965,541 filed Oct. 22, 1991, Jun. 4, 1992 and Nov. 2, 1992, respectively, and entitled "Adenosine Diphosphoribose Polymerase Binding Nitroso Aromatic Compounds Useful As Retroviral Inactivating Agents, Anti-retroviral Agents and Anti-tumor Agents;" various iodo-nitro compounds and iodo-nitroso compounds, which are the subject of copending U.S. patent application Ser. No. 08/060,409 filed on May 12, 1993, entitled "Novel Aromatic Nitro Compounds and Their Metabolites Useful as Anti-Viral and Anti-Tumor Agents," and U.S. patent application Ser. No. 08/076,313 filed Jun. 11, 1993, entitled "Novel Aromatic Nitro and Nitroso Compounds and Their Metabolites Useful as Anti-Viral and Anti-Tumor Agents," the disclosures of which are incorporated herein by reference.

These drugs are of remarkably low toxicity, yet highly effective inhibitors of tumors and viral replication in cell cultures. Their therapeutic spectrum appears to be particularly useful for suppression and inhibition of cancer growth and the treatment of viral infections.

The mechanisms of action of poly (ADP ribose) transferase polymerizing ("pADPRT") CCHC-oxidizing ligands such as aromatic C-nitroso compounds have been recently elucidated. Kun et al., Biochemie, in press (1994). One level comprises inactivation of pADPRT by zinc ejection. Recently published experiments have shown that aromatic C-nitroso ligands of pADPRT preferentially destabilize one of the two zinc fingers of the enzyme coincidentally with a loss of enzymatic activity but not DNA binding capacity of the protein. Buki et al., FEBS Lett. 290:181–185 (1991). Based on the similarity to results obtained by site-directed mutagenesis, Gradwohl et al., Proc. Natl. Sci. USA 87:2990–2992 (1990), it appears that the primary attack of C-nitroso ligands occurred at zinc finger F1, Buki et al., FEBS Lett. 290:181–185 (1991). 6-nitroso-1,2 benzopyrone ("NOBP") and 3-nitrosobenzamide ("NOBA"), two C-nitroso compounds that inactivate pADPRT at one zinc finger site completely suppressed the proliferation of leukemic and other malignant human cells and subsequently produced cell death. Tumoricidal concentrations of the drugs were relatively harmless to normal bone marrow progenitor cells and to superoxide formation by neutrophil granulocytes. The cellular mechanisms elicited by the C-nitroso compounds consists of apoptosis due to DNA degradation by the nuclear calcium/magnesium dependent endonuclease. Rice, et al. Proc. Natl. Sci. USA 89:7703–7707 (1992). This endonuclease is maintained in a latent form by poly(ADP-ribosyl)ation, but inactivation of pADPRT by C-nitroso drugs de-represses the DNA-degrading activity.

In contrast to the "classical" zinc finger structures identified in a large number of transcription factors where the zinc ligands are CCCC or CCHH, Klug and Rhodes, Trends in Biochem. Sci. 12:464–469 (1987), pADPRT contains two zinc chelates that are asymmetrical, i.e. the ligands are CCHC, Gradwohl et al., Proc. Natl. Acad. Sci. 87:2990–2994 (1990). This seemingly minor modification of the chelate has significant chemical consequence with respect to its stability as it exists in the zinc finger within the protein molecule. Buki et al., FEBS Lett. 290:181–185 (1991). Whereas CCCC or CCHH zinc fingers require basic pH and organomercurials to release zinc ion, Giedroc et al., J. Inorg. Biochem. 28:155–169 (1986), zinc ion exchange between the CCHC zinc fingers of pADPRT and external zinc under physiological circumstances, and oxidative destruction of the CCHC chelates by relatively mild oxidizing agents that are made selective by also being ligands of pADPRT has been demonstrated, Buki et al., FEBS Lett. 290:181–185 (1991). This represents a significant biochemical correlation. The F1 finger, Gradwohl et al., Proc. Natl. Acad. Sci. 87:2990–2994 (1990), of pADPRT is first inactivated by the oxidative ligands, resulting in a loss of DNA-stimulated pADPRT activity without major alterations of the DNA binding ability of pADPRT, but excess oxidant destroys both zinc fingers, Buki et al., FEBS Lett. 290:181–185 (1991).

The second level of activity comprises induction of an pADPRT-degrading aminopeptidase that completely digests pADPRT, whereby the pADPRT-binding sites on DNA become available to endonucleolytic degradation. Kun et al., Biochemie, in press (1994). Auto-poly-ADP-ribosylation protects pADPRT from digestion of aminopeptidase, hence inactivation of poly-ADP-ribosylation (as by aromatic C-nitroso ligands) is a prerequisite to proteolytic pADPRT degradation, leading to apoptosis. Therefore, pADPRT CCHC-oxidizing ligand, such as C-nitroso compounds, are effective anti-tumor compounds.

Retroviral nucleocapsid ("NC") proteins and their respective gag precursors from all strains of known retroviruses contain at least one copy of a zinc-binding polypeptide sequence of the type $Cys-X_2-Cys-X_4-His-X_4-Cys$ ("CCHC"), i.e., a zinc finger domain. Henderson et al., Biol. Chem. 256:8400–8406 (1981). This CCHC sequence is essential for maintaining viral infectivity, Gorelick et al., Proc. Natl. Acad. Sci. USA 85:8420–8424 (1988) and Gorelick et al., J. Virol. 64:3207–3211 (1990), therefore, it represents an attractive target for viral chemotherapy. The HIV-1 gag proteins function by specifically binding to the HIV-1 RNA, anchoring it to the cell membrane for budding of viral particles. Meric et al., J. Virol. 63:1558–1658 (1989); Gorelick et al., Proc. Natl. Acad. Sci. USA 85:8420–8424 (1988); Aldovini et al., J. Virol.

64:1920–1926 (1990); and Lever et al., *J. Virol.* 63:4085–4087 (1989). Site-directed mutagenesis studies demonstrated that modification of Cys or His residues results in defective viral RNA packaging and noninfectious viral particles are formed. Aldovini et al., *J. Virol.* 64:1920–1926 (1990) and Lever et al., *J. Virol.* 63:4085–4087 (1989).

Based on the occurrence of CCHC zinc binding sites in both retroviral nucleocapsid and gag-precursor proteins and in poly(ADP-ribose) polymerase it was reasoned that pADPRT CCHC-oxidizing ligands may also have anti-retroviral effects. Recently it was demonstrated that NOBA and NOBP inhibit infection of human immunodeficiency virus HIV-1 in human lymphocytes and also eject zinc from isolated HIV-1 NC zinc fingers and from intact HIV-1 virions. U.S. Ser. No. 0/087,566 filed Jul. 2, 1993; U.S. Ser. No. 08/076,313 filed Jun. 11, 1993; Rice et al., *Nature* 361:473–475 (1993); Rice et al., *Prac. Natl. Acad. Sci.* 90:9721–9724 (1993); Chuang et al., *FEBS Lett.* 326:140–144 (1993); and Wondrak et al., *J. Biol. Chem.* in press (1994). The zinc-ejected HIV-1 virions exhibit complete loss of infectivity in human lymphocytes. U.S. Ser. No. 0/087,566 filed Jul. 2, 1993 and U.S. Ser. No. 08/076,313 filed Jun. 11, 1993. It was of special interest that the infectious cycle of AZT-resistant rhesus macaque (MMU-23740)-derived SIV was equally inhibited by NOBA, Chuang et al., *FEBS Lett.* 326:140–144 (1993), an observation that is particularly relevant to opioid drug abusers where addiction coincides with the emergence of AZT resistance, Chuang et al., *NIDA Res. Monograph: Problems of Drug Dependence* 14:419 (1993). Therefore, the pADPRT CCHC-oxidizing ligands are effective anti-viral compounds.

While these C-nitroso pADPRT CCHC-oxidizing ligands have been found to be quite effective in in vitro tests, they are relatively water insoluble at physiological pH, exhibit limited stability and limited predictability of delivery to the affected cells due to their solubility and stability characteristics. In addition, the relative chemical instability of aromatic C-nitroso pADPRT CCHC-oxidizing ligands towards glutathione ("GSH") is a distinct disadvantage for their direct application in vivo. Recently precursor molecules which generate active C-nitroso compounds in vivo have been prepared to overcome some of these difficulties.

One recently prepared precursor, a cysteine sulfinic adduct of 3-nitrosobenzamide, releases the C-nitroso molecule at weakly basic conditions. Kun et al., U.S. Pat. No. 5,262,564 issued on Nov. 16, 1993. This sulfinic adduct is an effective C-nitroso donor molecule in cell cultures. Id.

As an alternative method, stable precursor C-nitro molecules which serve as pro-drugs for the active C-nitroso pADPRT CCHC-oxidizing ligands were recently prepared. U.S. patent application Ser. No. 08/076,313 filed on Jun. 11, 1993, which is incorporated herein by reference. A prototype of these pro-drugs, 4-iodo-3-nitrobenzamide ("$INO_2BA$") has been shown to be stable, having a shelf life of at least one year. Mendeleyev et al., "Chemotherapeutic Activity of 4-Iodo-3-Nitrobenzamide I: Metabolic Reduction to the 3-Nitroso Derivative and Induction of Apoptosis in Tumor Cells in Culture," submitted (1994) (hereinafter "Mendeleyev et al. (1994).")

The aromatic iodo-nitro pro-drugs are slowly but steadily enzymatically reduced within cells to the active aromatic iodo-nitroso compounds such that tumor cell apoptosis or inactivation of viral replication is induced. Id. See also Chuang et al., *Biochemical Pharmacology*, submitted (1995). These aromatic iodo-nitro compounds thus provide a ready source of in vivo anti-tumor C-nitroso compounds.

On the benzene ring, ortho-iodo-substitution has been shown to facilitate the electrochemical reduction of the nitro group. Fry, *The Chemistry of Amino, Nitroso and Nitro Compounds and Their Derivatives. Part I.*, S. Patai, ed., 319–335, John Wiley and Sons, N.Y. (1982). Recently the fluoro-, chloro- and bromo-analogues of $INO_2BA$ were tested for anti-tumor activity. These analogues were less effective than $INO_2BA$. Mendeleyev et al. (1994). Unsubstituted nitrobenzamides are at least 10–15 times less effective than $INO_2BA$. Id. Thus, it is highly probable that the metabolic reduction of aromatic iodo-nitro compounds in cells is activated by the presence of the iodo group ortho to the nitro group. Id.

It is known that glutathione adds to aromatic nitroso compounds to form labile semimercaptal adducts. Eyer, *Chem. Biol. Interactions* 24:227–239 (1979); Umemoto et al., *Chem. Biol. Interactions* 68:57–69 (1988); Ellis et al., *Chem. Biol. Interactions* 82:151–163 (1992). The semimercaptals undergo oxygen atom migration to yield sulfinimides that hydrolyze to the corresponding aromatic amines plus glutathione sulfinic acid. In addition, it has recently been shown that both NOBA and 4-iodo-nitrosobenzamide ("INOBA") are rapidly reduced to the corresponding hydroxyl amines by GSH and ascorbate in in vitro chemical tests. Since many cell types produce GSH, these reduction pathways can quickly reduce the active C-nitroso compounds available in vivo, thereby diminishing the efficacy of the C-nitroso compounds in vivo.

It was thus reasoned that agents which decrease intracellular levels of GSH ("GSH decreasing agents") would decrease the rate at which the active C-nitroso ligands are reduced to the corresponding amines in the cell. Recently, it has been shown that DL-buthionine sulfoximine ("BSO"), an agent that inhibits GSH biosynthesis, Meister, *Pharmacology and Therapeutics* 51:155–194 (1991), exhibits synergistic apoptosis-inducing potency when administered in combination with pADPRT CCHC-oxidizing ligands in several types of cancer cells. Mendeleyev et al. (1994). BSO also exhibited synergistic anti-viral activity when administered in combination with pADPRT CCHC-oxidizing ligands in cells infected with SIV. Chuang et al., "Chemotherapeutic Activity of 4-Iodo-3-Nitrobenzamide and 5-Iodo-6-Amino-Benzopyrone on Simian Immunodeficiency Virus (SIV) in Cultures of CEM ×174 Cells," submitted (1994) (hereinafter "Chuang et al. (1994)").

It is therefore a primary object of this invention to provide stable, soluble, non-toxic, highly effective antineoplastic and/or anti-viral synergistic compositions that inactivate pADPRT and NC p7 zinc fingers oxidatively.

pADPRT ligands that oxidize CCHC zinc fingers are not unique inhibitors of pADPRT. Inhibitory ligands of pADPRT that do not attack zinc have been identified. Such a prototype ligand, 6-amino-1,2-benzopyrone has been shown to have anti-tumor effects. Hakam et al., *FEBS Lett.* 193:1–4 (1991). These ligands bind non-covalently to the nicotinamide site and internal DNA-seeking domains of pADPRT. Bauer et al., manuscript in preparation (1994). In contrast, CCHC-oxidizing ligands also bind non-covalently to the nicotinamide site, but initially attack the F1 zinc finger oxidatively. Id. The respective molecular pharmacological action of both of these types of pADPRT-inhibitory ligands has been studied in a bovine endothelial cell line that has been transfected and transformed with E-ras and, by cellular cloning, the tumorigenic phenotype has been isolated. Id. Synergistic cytocidal effects of pADPRT CCHC-oxidizing ligands in combination with non-covalent pADPRT-inhibitory ligands has been demonstrated. U.S. Ser. No. 08/076,313 filed Jun. 11, 1993.

pADPRT ligands that oxidize CCHC zinc fingers are also not unique as potential anti-HIV drugs at the DNA level. Ligands of pADPRT that do not attack zinc fingers were also shown to be anti-retroviral, Cole et al., *Biochem. Biophys. Res. Commun.* 180:504–514 (1991), by mechanisms that relate to the drug-induced binding of pADPRT to either the reverse transcriptase template, Buki et al., *Biochem. Biophys. Res. Commun.* 180:496–503 (1991), or probably to transcription factors required for retroviral synthesis.

A prototypical molecule, 5-iodo-6-amino-1,2-benzopyrone ("IABP") blocked the infectious cycle of HIV as tested in various cell lines, Cole et al., *Biochem Biophys. Res. Commun.* 180:504–514 (1991), but had no influence on the CCHC zinc fingers of pADPRT or on the p7 NC protein of retroviruses. Thus, reversible inhibition of pADPRT as well as covalent inactivation of pADPRT by zinc ejection can abrogate HIV or SIV infection, in addition to a direct effect of the pADPRT CCHC-oxidizing ligands on the retroviral zinc fingers of the virion p7, Rice et al., *Nature* 361:473–475 (1993) and Wondrak et al., *J. Biol. Chem.* 269:21948–21950 (1994), pointing to a hitherto unrecognized role of pADPRT in the life cycle of retroviruses.

Based on this newly recognized role of pADPRT on the retroviral life cycle and the observance of synergy between pADPRT CCHC-oxidizing ligands in combination with non-covalent pADPRT-inhibitory ligands in cancer cells, it was reasoned that non-covalent ligands of pADPRT in combination with CCHC-oxidizing ligands would increase anti-retroviral activity as compared to such ligands acting independently.

It is therefore also a primary objective of this invention to provide non-toxic, highly effective anti-tumor and/or anti-viral synergistic compositions that inactivate pADPRT and NC p7 zinc fingers oxidatively, and that also inhibit pADPRT non-covalently.

SUMMARY OF THE INVENTION

The subject invention provides for novel synergistic anti-tumor and/or anti-retroviral compositions comprising one or a plurality of pADPRT CCHC-oxidizing ligands in combination with one or a plurality of agents selected from the group consisting of: GSH decreasing agents and non-covalent pADPRT-inhibitory ligands.

In one embodiment the subject invention provides for novel synergistic anti-tumor and/or anti-retroviral compositions comprising one or a plurality of pADPRT CCHC-oxidizing ligands such as nitro-estradiol, iodo-nitro-estradiol, nitroso-estradiol, iodo-nitroso-estradiol, nitro-estrone, iodo-nitro-estrone, nitroso-estrone, iodo-nitroso-estrone, nitro-estriol, iodo-nitro-estriol, nitroso-estriol, iodo-nitroso-estriol, nitro-equilenin, iodo-nitro-equilenin, nitroso-equilenin, iodo-nitroso-equilenin, nitro-equilin, iodo-nitro-equilin, nitroso-equilin, iodo-nitroso-equilin, nitro-diethylstilbestrol, iodo-nitro-diethylstilbestrol, nitroso-diethylstilbestrol, iodo-nitroso-diethylstilbestrol, nitrobenzamides, nitrosobenzamides, iodo-nitro-benzamides, iodo-nitrosobenzamides, 4-iodo-3-nitrobenzamide, 4-iodo-3-nitrosobenzamide, 2-iodo-5-nitrobenzamide, 2-iodo-5-nitrosobenzamide, nitro-1,2-benzopyrones, nitroso-1,2-benzopyrones, 6-nitro-1,2-benzopyrones, 6-nitroso-1,2-benzopyrones, iodo-nitro-1,2-benzopyrones, iodo-nitroso-1,2-benzopyrones, 4-iodo-3-nitro-1,2-benzopyrone, 4-iodo-3-nitroso-1,2-benzopyrone, 5-iodo-6-nitro-1,2-benzopyrone, 5-iodo-6-nitroso-1,2-benzopyrone, nitro-isoquinolinones, iodo-nitro-isoquinolinones, nitroso-isoquinolinones, iodo-nitroso-isoquinolinones, 5-nitro-1(2H)-isoquinolinone, iodo-5-nitro-1(2H)-isoquinolinones, 5-nitroso-1(2H)-isoquinolinone, iodo-5-nitroso-1(2H)-isoquinolinones, 7-nitro-1(2H)-isoquinolinone, iodo-7-nitro-1(2H)-isoquinolinone, 7-nitroso-1(2H)-isoquinolinone, odo-7-nitroso-1(2H)-isoquinolinones, 8-nitro-1(2H)-isoquinolinone, iodo-8-nitro-1(2H)-isoquinolinone, 8-nitroso-1(2H)-isoquinolinone, iodo-8-nitroso-1(2H)-isoquinolinones and their homologues, in combination with a one or a plurality of GSH decreasing agents such as BSO and diethylmaleate.

In another embodiment the subject invention also provides for novel synergistic anti-tumor and/or anti-viral compositions comprising one or a plurality of pADPRT CCHC-oxidizing ligands such as nitro-estradiol, iodo-nitro-estradiol, nitroso-estradiol, iodo-nitroso-estradiol, nitro-estrone, iodo-nitro-estrone, nitroso-estrone, iodo-nitroso-estrone, nitro-estriol, iodo-nitro-estriol, nitroso-estriol, iodo-nitroso-estriol, nitro-equilenin, iodo-nitro-equilenin, nitroso-equilenin, iodo-nitroso-equilenin, nitro-equilin, iodo-nitro-equilin, nitroso-equilin, iodo-nitroso-equilin, nitro-diethylstilbestrol, iodo-nitro-diethylstilbestrol, nitroso-diethylstilbestrol, iodo-nitroso-diethylstilbestrol, nitrobenzamides, nitrosobenzamides, iodo-nitro-benzamides, iodo-nitrosobenzamides, 4-iodo-3-nitrobenzamide, 4-iodo-3-nitrosobenzamide, 2-iodo-5-nitrobenzamide, 2-iodo-5-nitrosobenzamide, nitro-1,2-benzopyrones, nitroso-1,2-benzopyrones, 6-nitro-1,2-benzopyrones, 6-nitroso-1,2-benzopyrones, iodo-nitro-1,2-benzopyrones, iodo-nitroso-1,2-benzopyrones, 4-iodo-3-nitro-1,2-benzopyrone, 4-iodo-3-nitroso-1,2-benzopyrone, 5-iodo-6-nitro-1,2-benzopyrone, 5-iodo-6-nitroso-1,2-benzopyrone, nitro-isoquinolinones, iodo-nitro-isoquinolinones, nitroso-isoquinolinones, iodo-nitroso-isoquinolinones, 5-nitro-1(2H)-isoquinolinone, iodo-5-nitro-1(2H)-isoquinolinones, 5-nitroso-1(2H)-isoquinolinone, iodo-5-nitroso-1(2H)-isoquinolinones, 7-nitro-1(2H)-isoquinolinone, iodo-7-nitro-1(2H)-isoquinolinone, 7-nitroso-1(2H)-isoquinolinone, iodo-7-nitroso-1(2H)-isoquinolinones, 8-nitro-1(2H)-isoquinolinone, iodo-8-nitro-1(2H)-isoquinolinone, 8-nitroso-1(2H)-isoquinolinone, iodo-8-nitroso-1(2H)-isoquinolinones and their homologues, in combination with a one or a plurality of non-covalent pADPRT-inhibitory ligands such as 1,2-benzopyrones, benzamides, amino-1,2-benzopyrones, amino-benzamides, 5-amino-1,2-benzopyrones, 3-aminobenzamides, amino-iodo-benzopyrones, amino-iodo-benzamides, 5-iodo-6-amino-1,2-benzopyrone, 4-iodo-3-aminobenzamides and their homologues.

The invention further provides for methods of treating cancer and viral diseases with such synergistic compositions.

Another aspect of the invention is to provide methods for inactivating viruses, especially retroviruses, in biological material, e.g. blood, by adding one or a plurality of synergistic compositions to the biological material.

Another aspect of the invention is to provide methods for inactivating AZT-resistant viruses, in particular HIV and SIV, by adding one or a plurality of synergistic compositions to a cell culture or mammalian host infected with an AZT-resistant virus.

Another aspect of the invention is to provide methods for inducing apoptosis in a tumor cell by administering one or a plurality of synergistic compositions to a cell culture or mammalian host having one or a plurality of tumors.

In a preferred embodiment of the invention the pADPRT CCHC-oxidizing ligands have an iodo group adjacent to the nitroso or nitro group. In an even more preferred mode the pADPRT CCHC-oxidizing ligands are aromatic C-nitro in vivo precursors of active C-nitroso ligands having an iodo group adjacent to a nitro group, including iodo-nitro-estradiol, iodo-nitro-estrone, iodo-nitro-estriol, iodo-nitro-equilenin, iodo-nitro-equilin, iodo-nitro-diethylstilbestrol, nitrobenzamides, iodo-nitro-benzamides, 4-iodo-3-nitrobenzamide, 2-iodo-5-nitrobenzamide, nitro-1,2-benzopyrones, 6-nitro-1,2-benzopyrones, iodo-nitro-1,2-benzopyrones, 4-iodo-3-nitro-1,2-benzopyrone, 5-iodo-6-nitro-1,2-benzopyrone, nitro-isoquinolinones, iodo-nitro-isoquinolinones and their homologues.

In another preferred embodiment of the invention the pADPRT-oxidizing ligands are selected from the group consisiting of 3-nitroso-benzamide, 4-iodo-3-nitroso-benzamide, 2-iodo-5-nitroso-benzamide, 3-nitro-benzamide, 4-iodo-3-nitro-benzamide, 2-iodo-5-nitro-benzamide, 6-nitroso-1,2-benzopyrone, 5-iodo-6-nitroso-1,2-benzopyrone, 6-nitro-1,2-benzopyrone, and 5-iodo-6-nitro-1,2-benzopyrone.

In yet another preferred embodiment of the invention the pADPRT CCHC-oxidizing ligands are selected from the group consisting of 4-iodo-3-nitro-benzamide, 2-iodo-5-nitro-benzamide and 5-iodo-6-nitro-1,2-benzopyrone.

In still another preferred embodiment of the invention the non-covalent pADPRT-inhibitory ligands are selected from the group consisting of 6-amino-1,2-benzopyrone and 5-iodo-6-amino-1,2-benzopyrone.

In yet another preferred embodiment of the invention the GSH reducing agents are selected from the group consisting of diethylmaleate and BSO.

DESCRIPTION OF THE FIGURES

FIG. 1 is a graph comparing the inactivation of pADPRT by NOBA and INOBA. pADPRT inactivation was performed in 20-μl volumes of buffer containing 50 mM Hepes (pH 7.4), 100 mM KCl, 0.5 mM EDTA, pADPRT (0.4 μg/μl) and different concentrations of inactivators. Inactivators were serially diluted in the above buffer from a 20 mM stock solution in DMF. The DMF concentration (2.5%) was kept constant in the inactivation mixes. After 2 hr. at 25° C., aliquots (3 μl) were removed for assay of enzyme activity in a volume of assay mix (200 μl) in which the inactivators were dilute enough not to act as inhibitors. The assay mix consisted of 100 mM Tris (pH 7.7), 14 mM 2-mercaptoethanol, 0.1 mM [$^{32}$P]-NAD$^+$, 0.2 mg/ml coDNA and 0.1 mg/ml histones. The result of the pADPRT assays are shown in FIG. 1. The incorporated $^{32}$P, proportional to enzyme activity, is plotted as percent of the untreated sample.

FIG. 2A is a graph comparing the effects of NOBA and INOBA on the enzyme activity and zinc content of pADPRT. Inactivation was performed as described in Example III. In these experiments $^{65}$Zn$^{2+}$-labeled pADPRT was used. The Zn$^{2+}$ content of pADPRT (upper panel) was determined as follows: two parallels of aliquots (4 μl) were pipetted into 500 μl of ice-cold washing solution (50 mM Tris, pH 7.7, 10 mM 2-mercaptoethanol and 0.5 mM EDTA) then filtered onto GF/C disks presoaked in washing solution (cold), quickly washed 4 times with 1 ml of ice-cold washing solution, dried, and the radioactivity determined. The protein-bound $^{65}$Zn$^{2+}$ is shown as percent of the untreated sample. Enzyme assays (lower panel) were performed as in FIG. 1.

FIG. 9B shows the synergistic effect of IABP in combination with $INO_2BA$ on the viability of SIVmac239-infected CEM ×174 cells. The procedure was the same as for FIG. 3A. The cell viability was measured by the MTT assay on day 10 of the experiment. The effect of $INO_2BA$ alone is shown in the front columns, and the two drugs in combination in the rear columns.

DESCRIPTION OF SPECIFIC EMBODIMENTS

Definitions

Figure 2B:
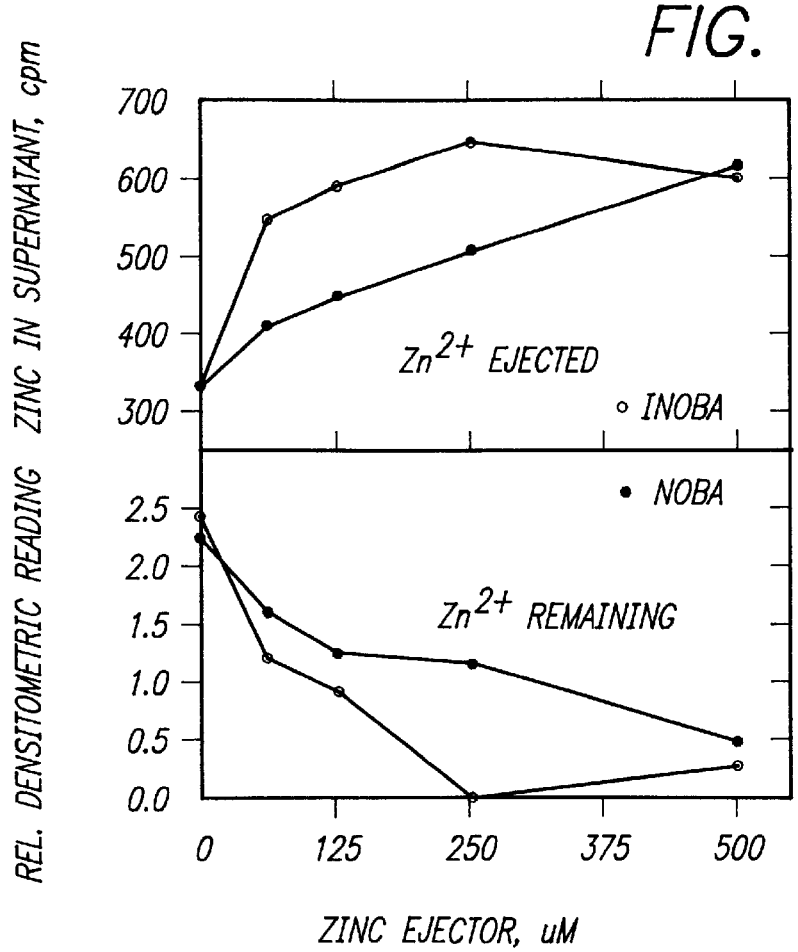
FIG. 2B shows the release of pADPRT zinc effected by NOBA and INOBA. For the release of Zn$^{2+}$ from transblotted pADPRT, the enzyme (3 μg per lane) was separated on SDS-PAGE, transblotted onto a nitrocellulose membrane, and renatured in the presence of $^{65}$ZnCl$_2$. The Zn$^{2+}$-loaded transblot was cut into strips and incubated with 2 ml of 50 mM Hepes/NaOH (pH 7.0) and 0.5 mM EDTA containing different concentrations of either NOBA or INOBA as indicated, for 2 hr. at 25° C. After incubation, 1 ml of the supernatant was counted for radioactivity, and the strips were washed 3 times with 2 ml of 50 mM Tris-HCl pH 7.4), 0.5 mM EDTA and 10 Mm 2-mercaptoethanol, and then dried and exposed to X-ray film. The intensity of the autoradiographic spots was quantitated by a scanner.

As used herein:

"Biological Material" refers to any biological material extracted from a living organism, including blood, plasma, cerebrospinal fluid, organs, and the like, as well as the processed products of biological material extracted from a living organism.

"Zinc Finger" refers to a structural domain of a protein capable of binding a zinc atom. The nature of zinc finger protein domains is well described in the literature, e.g., Klug and Rhodes, *Trends in Biochemical Sciences* 12:464–469 (1987).

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"pADPRT" refers to adenosinediphosphoribose transferase also known as poly (ADP-ribose)polymerase, (EC 2.4.30), a specific DNA-binding nuclear protein of eucaryotes that catalyzes the polymerization of ADP-ribose. The enzymatic process is dependent on DNA.

"pADPRT CCHC-oxidizing ligands" refers to aromatic C-nitroso compounds that bind to the CCHC zinc finger of pADPRT and effect zinc ejection. pADPRT CCHC-oxidizing ligands also refers to C-nitro precursors of active aromatic C-nitroso compounds. Such ligands include, but are not limited to, nitro-estradiol, iodo-nitro-estradiol, nitroso-estradiol, iodo-nitroso-estradiol, nitro-estrone, iodo-nitro-estrone, nitroso-estrone, iodo-nitroso-estrone, nitro-estriol, iodo-nitro-estriol, nitroso-estriol, iodo-nitroso-estriol, nitro-equilenin, iodo-nitro-equilenin, nitroso-equilenin, iodo-nitroso-equilenin, nitro-equilin, iodo-nitro-equilin, nitroso-equilin, iodo-nitroso-equilin, nitro-diethylstilbestrol, iodo-nitro-diethylstilbestrol, nitroso-diethylstilbestrol, iodo-nitroso-diethylstilbestrol, nitrobenzamides, nitrosobenzamides, iodo-nitro-benzamides, iodo-nitrosobenzamides, 4-iodo-3-nitrobenzamide, 4-iodo-3-nitrosobenzamide, 2-iodo-5-nitrobenzamide, 2-iodo-5-nitrosobenzamide, nitro-1,2-benzopyrones, nitroso-1,2-benzopyrones, 6-nitro-1,2-benzopyrones, 6-nitroso-1,2-benzopyrones, iodo-nitro-1,2-benzopyrones, iodo-nitroso-1,2-benzopyrones, 4-iodo-3-nitro-1,2-benzopyrone, 4-iodo-3-nitroso-1,2-benzopyrone, 5-iodo-6-nitro-1,2-benzopyrone, 5-iodo-6-nitroso-1,2-benzopyrone, nitro-isoquinolinones, iodo-nitro-isoquinolinones, nitroso-isoquinolinones, iodo-nitroso-isoquinolinones, 5-nitro-1(2H)-isoquinolinone, iodo-5-nitro-1(2H)-isoquinolinones, 5-nitroso-1(2H)-isoquinolinone, iodo-5-nitroso-1(2H)-isoquinolinones, 7-nitro-1(2H)-isoquinolinone, iodo-7-nitro-1(2H)-isoquinolinone, 7-nitroso-1(2H)-isoquinolinone, iodo-7-nitroso-1(2H)-isoquinolinones, 8-nitro-1(2H)-isoquinolinone, iodo-8-nitro-1(2H)-isoquinolinone, 8-nitroso-1(2H)-isoquinolinone, iodo-8-nitroso-1(2H)-isoquinolinones and their homologues.

"GSH Decreasing Agent" refers to agents that decrease cellular levels of glutathione. Examples include, but are not limited to diethylmaleate and BSO.

"Non-covalent pADPRT-inhibitory ligands" refers to compounds that bind non-covalently to the nicotinamide site of pADPRT, but that do not attack the F1 zinc finger of pADPRT oxidatively. Examples of such ligands include, but are not limited to, 1,2-benzopyrones, benzamides, amino-1,2-benzopyrones, amino-benzamides, 6-amino-1,2-benzopyrones, 3-amino-benzamide, amino-iodo-benzopyrones, amino-iodo-benzamides, 5-iodo-6-amino-1,2-benzopyrone, 4-iodo-3-amino-benzopyrone and their homologues.

"Alkyl" refers to saturated or unsaturated branched or straight chain hydrocarbon radical. Typical alkyl groups includes methyl, ethyl, propyl, isopropyl, butyl, isobutyl, tertiary butyl, pentyl, hexyl and the like.

"Alkoxy" refers to the radical -0-alkyl. Typical alkoxy radicals are methoxy, ethoxy, propoxy, butoxy and pentoxy and the like.

"Cycloalkyl" refers to a saturated monocyclic hydrocarbon radical containing 3–8 carbon atoms such as cyclopropyl, cyclobutyl, cyclopentyl, cyclohexyl, cycloheptyl and cyclooctyl.

"Substituted phenyl" refers to all possible isomeric phenyl radicals mono or di-substituted with a substituent selected from the group consisting of alkyl, alkoxy, hydroxy or iodo.

The subject invention provides for novel synergistic compositions that find use as anti-tumor or anti-viral compositions. In one embodiment of the invention, the synergistic compositions comprise one or a plurality of pADPRT CCHC-oxidizing ligands in combination with one or a plurality of agents selected from the group consisting of agents that decrease cellular levels of glutathione and non-covalent pADPRT-inhibitory ligands.

In another embodiment of the invention the synergistic compositions comprise one or a plurality of pADPRT CCHC-oxidizing ligands in combination with one or a plurality of GSH decreasing agents.

In yet another embodiment of the invention the synergistic compositions comprise one or a plurality of pADPRT CCHC-oxidizing ligands in combination with one or a plurality of non-covalent pADPRT-inhibitory ligands.

The pADPRT CCHC-oxidizing ligands of the subject invention are described by the formulae below:

Compound I has the following formula:

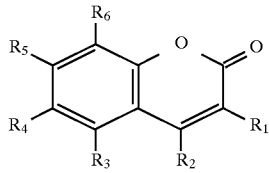
(I)

wherein $R_1$, $R_2$, $R_3$, $R_4$, $R_5$ and $R_6$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen and wherein at least one of the six $R_1$, $R_2$, $R_3$, $R_4$, $R_5$ and $R_6$ substituents is nitroso or nitro.

Compound II has the formula:

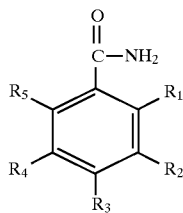
(II)

wherein $R_1$, $R_2$, $R_3$, $R_4$ and $R_5$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are hydrogen and wherein at least one of the five $R_1$, $R_2$, $R_3$, $R_4$, and $R_5$ substituents is nitroso or nitro.

Compound III has the formula:

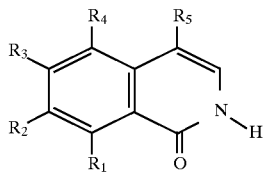
(III)

wherein $R_1$, $R_2$, $R_3$, $R_4$ and $R_5$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are hydrogen and wherein at least one of the five $R_1$, $R_2$, $R_3$, $R_4$, and $R_5$ substituents is nitroso or nitro.

Compound IV has the formula:

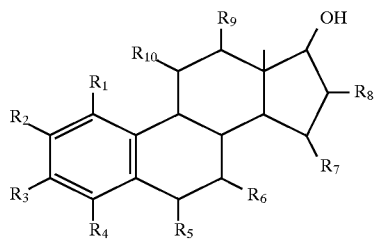
(IV)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

Compound V has the formula:

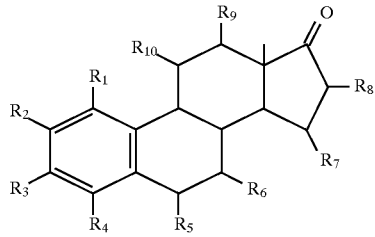
(V)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

Compound VI has the formula:

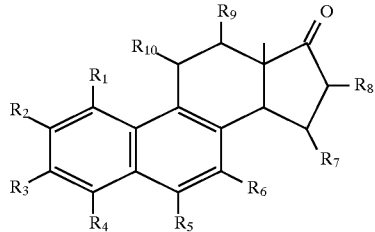
(VI)

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

Compound VII has the formula:

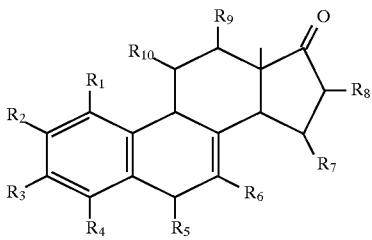

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_6$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

Compound VIII has the formula:

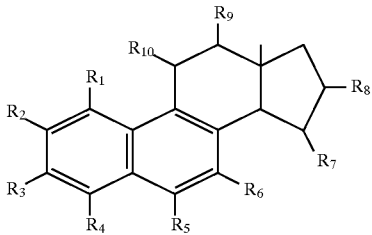

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

Compound IX has the formula:

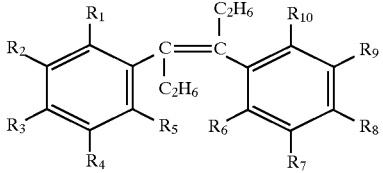

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten $R_1$, $R_2$, $R_3$, $R_4$, $R_5$, $R_6$, $R_7$, $R_8$, $R_9$ and $R_{10}$ substituents are hydrogen and wherein at least one of the ten $R_1$, $R_2$, $R_3$, $R_4$, $R_5$, $R_6$, $R_7$, $R_8$, $R_9$ and $R_{10}$ substituents is nitroso or nitro.

In a preferred preferred embodiment, compounds of formulae I–IX have an iodo group attached adjacent to a nitroso or nitro group.

In a more preferred embodiment, compounds of formulae I–IX have an iodo group attached adjacent to a nitro group.

In another preferred embodiment, the pADPRT CCHC-oxidizing ligands are selected from the group consisting of a compound according to formula I and a compound according to formula II.

In another preferred embodiment the pADPRT CCHC-oxidizing ligands are selected from the group consisting of 3-nitroso-benzamide, 4-iodo-3-nitroso-benzamide, 2-iodo-5-nitroso-benzamide, 3-nitro-benzamide, 4-iodo-3-nitro-benzamide, 2-iodo-5-nitro-benzamide, 6-nitroso-1,2-benzopyrone, 5-iodo-6-nitroso-1,2-benzopyrone, 6-nitro-1,2-benzopyrone, and 5-iodo-6-nitro-1,2-benzopyrone.

In another preferred embodiment the pADPRT CCHC-oxidizing ligands are selected from the group consisting of 4-iodo-3-nitrobenzamide, 2-iodo-5-nitrobenzamide and 5-iodo-6-nitro-benzamide-1,2-benzopyrone.

Non-covalent pADPRT-inhibitory ligands of the subject invention are described by the formulae below:

Compound X has the formula:

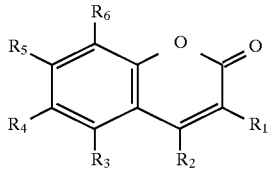

wherein $R_1$, $R_2$, $R_3$, $R_4$, $R_5$ and $R_6$ are, independent of one another, selected from the group consisting of hydrogen, hydroxy, amino, iodo, alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen.

Compound XI has the formula:

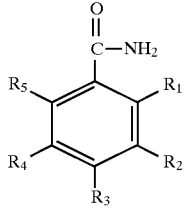

wherein $R_1$, $R_2$, $R_3$, $R_4$, $R_5$ and $R_6$ are, independent of one another, selected from the group consisting of hydrogen, hydroxy, amino, iodo, alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen.

In a preferred embodiment of the invention the non-covalent pADPRT-inhibitory ligands are selected from the group consisting of 6-amino-1,2-benzopyrone and 5-iodo-6-amino-1,2-benzopyrone.

GSH decreasing agents of the subject invention include, but are not limited to, BSO and diethylmaleate. In a preferred embodiment said GSH decreasing agents are selected from the group consisting of diethylmaleate and BSO.

Synergistic Anti-Tumor Activity of the Novel Compositions pADPRT CCHC-oxidizing ligands such as aromatic C-nitroso compounds are potent anti-tumorigenic drugs. The anti-tumorigenic activity of such compounds has been studied extensively and is described in the literature and in Example II. Aromatic C-nitro compounds are in vivo precursors of aromatic C-nitroso compounds. These in vivo precursors are reduced to the active C-nitroso ligand in vivo, supplying a readily available source of the active C-nitroso ligand in vivo. Such activity has been studied extensively in cell lines and is described in detail in Example II.

Example VI describes the metabolic conversion of $INO_2BA$ to 4-iodo-3-aminobenzamide ("$INH_2BA$") by 855-2 cells. A slow but steady reduction of the nitro compounds occurred at a rate of 2.2±0.2% per 18 hours of cell incubation at 37° C. Apart from trace metabolites, the only identifiable metabolite was 4-iodo-3-amino-benzamide ($INH_2BA$).

Example III illustrates the inactivation of pADPRT by NOBA and INOBA, with concomitant zinc ion ejection. As shown in the example, under comparable in vitro conditions INOBA was the more effective inactivator of pADPRT. Zinc ejection was complete within 2 hours for both NOBA and INOBA.

Example IX illustrates the synergistic effect of BSO in combination with $INO_2BA$ in various cancer cell lines. BSO in combination with $INO_2BA$ showed synergistic cytotoxic effects in all twelve of the cell lines tested.

Example VIII illustrates the synergistic effect of BSO with 4-iodo-3-nitrobenzoic acid, $INO_2BA$ and NOBA in Molt-4 and L-1210 cells. As shown in the example, treatment of Molt-4 and L-1210 cells with 1 mM BSO alone had no effect on cell growth over two days. Treatment of cells with 4-iodo-3-nitrobenzoic acid, $INO_2BA$ and NOBA alone also had no inhibitory effect on cell growth over two to three days. However, treatment with BSO in combination with the pADPRT CCHC-oxidizing ligands synergistically produced cell death of tumor cells.

Thus, as is demonstrated by the above, the exemplary compositions of BSO in combination with 4-iodo-3-nitrobenzoic acid, $INO_2BA$ and NOBA, respectively, resulted in synergistic cytotoxic effects in various cancer cell lines. Specifically, BSO increased the cytotoxicity of each of NOBA, $INO_2BA$ and 4-iodo-3-nitrobenzoic acid. The increased cytotoxicity in each case was more than additive.

Example XVII demonstrates the synergistic effect of IABP in combination with $INO_2BA$ in L 1210 cells.

Thus, as is demonstrated by the above, the exemplary composition of IABP in combination with $INO_2BA$ resulted in synergistic cytotoxic effects in L 1210 cells. Specifically, $INO_2BA$ increased the cytotoxicity of IABP and IABP increased the cytotoxicity of $INO_2BA$. The increased cytotoxicity in each case was more than additive.

Synergistic Anti-Retroviral Activity of the Novel Compositions pADPRT CCHC-oxidizing ligands are also potent anti-retroviral drugs. Such activity has been studied extensively and is described in Example XIII. Aromatic C-nitro compounds are in vivo precursors of active C-nitroso derivatives. These precursors are reduced in vivo to the active C-nitroso compound, providing a ready supply of the active C-nitroso compound in vivo. The anti-viral activity of such C-nitro precursors has been studied and is described in Example XI.

While the C-nitro pro-drug had no effect on SIV infectivity, its intra-cellular metabolite readily inhibits SIV propagation. A further advantage of the pro-drug is that it is effective even after viral infection, whereas the C-nitroso drug requires pre-incubation of cells prior to viral infection, as is demonstrated in Example XV.

Example XIV illustrates the effect of various concentrations of $INO_2BA$ alone and in combination with various concentrations of BSO on the viability of SIV-infected CEM ×174 cells.

Example XIV also shows the effect of various concentrations of $INO_2BA$ alone and in combination with various concentrations of BSO on SIV replication. As is demonstrated in the Example, BSO alone had no effect on SIV replication. A BSO concentration of 0.01 mM in combination with 50 $\mu$M and 100 $\mu$M $INO_2BA$ showed a synergistic effect on SIV replication activity. Both 0.05 and 0.25 mM BSO in combination with 25 $\mu$M, 50 $\mu$M and 100 $\mu$M $INO_2BA$ showed a synergistic effect on SIV replication activity.

Thus, as is demonstrated by the above, the exemplary composition of BSO in combination with $INO_2BA$ resulted in a potentiation effect on SIV replication.

Non-covalent pADPRT-inhibitory ligand IABP blocked the infectious cycle of HIV as tested in various cell lines. Cole et al., Biochem Biophys. Res. Commun. 180:504–514 (1991).

The molecular mode of action of pADPRT CCHC-oxidizing ligands is clearly different from that of non-covalent pADPRT-inhibitory ligands. See Rice et al., Nature 361:473–475 (1993); Chuang et al., FEBS Lett. 326:140–144 (1993); Rice et al., Proc. Natl. Acad. Sci. 90:9721–9724 (1993); and Cole et al., Biochem Biophys. Res. Commun. 180:504–514 (1991). That the modes of action of pADPRT CCHC-oxidizing ligands and non-covalent pADPRT ligands are different is illustrated in Example XIII. Example XIII shows that depletion of cellular GSH by BSO, an inhibitor of γ-glutamyl cysteine synthetase, Meister, Science 220:472–477 (1991), synergistically enhances the inhibitory effect of INOBA and $INO_2BA$ on SIV replication in CEM ×174 cells. Since IABP was insensitive to addition of BSO, Chuang et al., submitted (1994), the molecular modes of action of the pADPRT CCHC-oxidizing ligands and non-covalent pADPRT ligands are clearly differentiated.

Example XVIII shows the inhibitory effect of IABP on SIVmac239 replication. As is clear from the example, both 0.3 and 0.5 mM IABP reduced the titre of virions in the supernatant of the cultures.

The synergistic effect of the pADPRT CCHC-oxidizing ligand $INO_2BA$ in combination with the non-covalent pADPRT ligand IABP on the replication of SIV is illustrated in Example XIX. As is shown in the Example, a more than additive anti-HIV action of 0.3 mM IABP and varying concentrations of $INO_2BA$, as assayed by the inhibition of p27 formation in CEM ×174 cells infected with SIVmac239, was observed. This drug combination also supported cell growth more than additively.

The non-toxicity of the non-covalent pADPRT-inhibitory ligand IABP is shown in Example XX.

Administration

In carrying out the methods of the present invention, the synergistic compositions will be administered in amounts which will be sufficient to kill cancer cells or inhibit retroviral expression or infection in the host in the pharmaceutical form most suitable for such purposes.

Administration of the synergistic compositions and salts described herein can be via any of the accepted modes of administration for therapeutic agents. These methods include systemic or local administration such as oral, parenteral, transdermal, subcutaneous, or topical administration modes. The preferred method of administration of these compositions is intravenous, except in those cases where the subject has topical tumors or lesions, where the topical administration may be proper. In other instances, it may be necessary to administer the compositions in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. In one embodiment the compositions will include an effective amount of one or a plurality of pADPRT CCHC-oxidizing ligands of formulae I–IX, or the pharmaceutically acceptable salts thereof, in combination with one or a plurality of GSH decreasing agents and in addition, it may include any conventional pharmaceutical excipients and other medicinal or pharmaceutical drugs or agents, carriers, adjuvants, diluents, etc., as is customary in the pharmaceutical sciences.

In another embodiment the compositions will include an effective amount of one or a plurality of pADPRT CCHC-oxidizing ligands of formulae I–IX, or the pharmaceutically acceptable salts thereof, in combination with one or a plurality of non-covalent pADPRT-inhibitory ligands of formulae X–XI, or the pharmaceutically acceptable salts thereof, and in addition it may include any conventional pharmaceutical excipients and other medicinal or pharmaceutical drugs or agents, carriers, adjuvants, diluents, etc., as is customary in the pharmaceutical sciences.

For solid compositions such excipients include pharmaceutical grades of mannitol, lactose, starch, magnesium stearate, sodium saccharin, talcum, cellulose, glucose, sucrose, magnesium carbonate, and the like may be used. The synergistic pharmaceutical compositions may be also formulated as suppositories using, for example, polyalkylene glycols, for example, propylene glycol, as the carrier.

Liquid, particularly injectable pharmaceutical compositions can, for example, be prepared by dissolving, dispersing, etc., an effective amount of one or a plurality of pADPRT CCHC-oxidizing ligands of formulae I–IX, or the pharmaceutically acceptable salt thereof, in combination with an effective amount of one or a plurality of GSH decreasing agents or in combination with an effective amount of one or a plurality of non-covalent pADPRT-inhibitory ligands, or the pharmaceutically acceptable salt thereof, in a pharmaceutical solution such as, for example, water, saline, aqueous dextrose, glycerol, ethanol, and the like, to thereby form the injectable solution or suspension.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

If desired, the pharmaceutical composition to be administered may contain liposomal formulations comprising a phospholipid, a negatively charged phospholipid and a compound selected from cholesterol, a fatty acid ester of cholesterol or an unsaturated fatty acid. The synergistic composition may be encapsulated or partitioned in a bilayer of liposomes of the liposomal formulation according to U.S. patent application Ser. No. 08/020,035 entitled "Liposomal Formulations and Methods of Making and Using Same" filed on Feb. 19, 1993 which is incorporated herein by reference.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow-release or sustained-released systems, which assures that a constant level of dosage is maintained, according to U.S. Pat. No. 3,710,795, which is incorporated herein by reference.

In one embodiment, such pharmaceutical generally compositions include about 1 to about 100 parts pADPRT CCHC-oxidizing ligands of formulae I–IX, or the pharmaceutically acceptable salts thereof, and about 200 to about 800 parts GSH decreasing agents mixed with a pharmaceutical excipient.

In one embodiment such pharmaceutical compositions include about 1 to about 100 parts pADPRT CCHC-oxidizing ligands of formulae I–IX, or the pharmaceutically acceptable salts thereof, and about 200 to about 800 parts non-covalent pADPRT-inhibitory ligands of formulae X–XI, or the pharmaceutically acceptable salts thereof, mixed with a pharmaceutical excipient.

Actual methods of preparing such dosage forms are known, or will be apparent to those skilled in this art, and are desired in detail described in *Remington's Pharmaceutical Sciences*, Mack Publishing Company, Easton, Pa., 17th Edition, 1985. The composition or formulation to be administered will, in any event, contain such quantity of the synergistic compositions that will assure that a therapeutically effective amount will be delivered to a patient. A therapeutically effective amount means an amount effective to prevent development of or to alleviate the existing symptoms of the subject being treated.

The amount of synergistic composition administered will, of course, be dependent on the subject being treated, on the subject's weight, the severity of the affliction, the manner of administration and the judgment of the prescribing physician. However, an effective dosage is one wherein one or a plurality of pADPRT CCHC-oxidizing ligands are administered in the range of 0.001 to 5000 mg/kg/day, preferably 0.01 to 1000 mg/kg/day, and more preferably 0.1 to 100 mg/kg/day.

Although the effective molar ratio of pADPRT CCHC-oxidizing ligands to GSH decreasing agents or to non-covalent pADPRT-inhibitory ligands comprising such synergistic compositions will vary in accordance with the nature of pADPRT CCHC-oxidizing ligands, non-covalent pADPRT-inhibitory ligands, GSH decreasing agents and particular subject, preferred molar ratios of pADPRT CCHC-oxidizing ligands to GSH decreasing agents are from about 1:1 to about 1:10, and more preferably from about 1:1 to about 1:100. Preferred effective molar ratios of pADPRT CCHC-oxidizing ligands to non-covalent pADPRT-inhibitory ligands are from about 1:1 to about 1:10, and more preferable from about 1:1 to about 1:100. Effective molar ratios may be readily determined by testing the effect of a range of concentrations of one or a plurality of C-nitroso pADPRT CCHC-oxidizing ligands in combination with a range of concentrations of GSH decreasing agents or non-covalent pADPRT-inhibitory ligands.

Generally, the upper limit for the drug dose determination is its efficacy balanced with its possible toxicity. Such toxicity appears to be very low for the pADPRT CCHC-oxidizing ligand prodrug $INO_2BA$ (hamsters injected daily intraperitoneally with 200 mg/kg for 12 days showed no toxic effects), for the non-covalent pADPRT-inhibitory ligand IABP, Cole et al., *Biochem Biophys. Res. Commun.* 180:504–514 (1991), and for BSO, Liebman et al., *Cancer Res.* 53:2066–2070 (1993); Yao et al., *Cancer Res.* 53:3662–3666 (1993); Terradez et al., *Biochem J.* 292:477–483 (1993); and Polhuijs et al., *Biochem J.* 285:401–404 (1992). Thus, the administered dose may be as high as needed to achieve desirable therapeutic effect.

Various substituents of the ligands as shown in formulae I–XI, are likely to modify lipid solubility or rate of cellular penetration, thus clinical dosage schedules of the synergistic compositions is likely to be altered on a molecular level by added substituents.

The chemotherapy may be repeated intermittently while tumors or HIV infections are detectable or even when they are not detectable.

Moreover, due to its apparent nontoxicity, the therapy may be provided alone or in combination with other antiviral or other drugs, such as for example AZT, anti-inflammatories antibiotics, corticosteroids, vitamins and other such drugs. There are no contraindications to use the synergistic compositions with even such toxic drugs as AZT since the synergistic compositions are nontoxic and their modes of action are quite different. Possible synergism between the synergistic compositions and other drugs is expected and predictable. In addition, possible synergism between a plurality of synergistic compositions of the present invention is also expected and predictable.

The synergistic compositions are equally useful for treatment of herpetic lesions caused by both HSV-1 and HSV-2. The compositions would be preferably administered by intravenous infusion or other parenteral or systemic mode of administration. In case of sores, the synergistic composition could also be administered topically. Infection caused by CMV would be treated preferably in the same fashion as that suggested for AIDS treatment.

Figure 8:
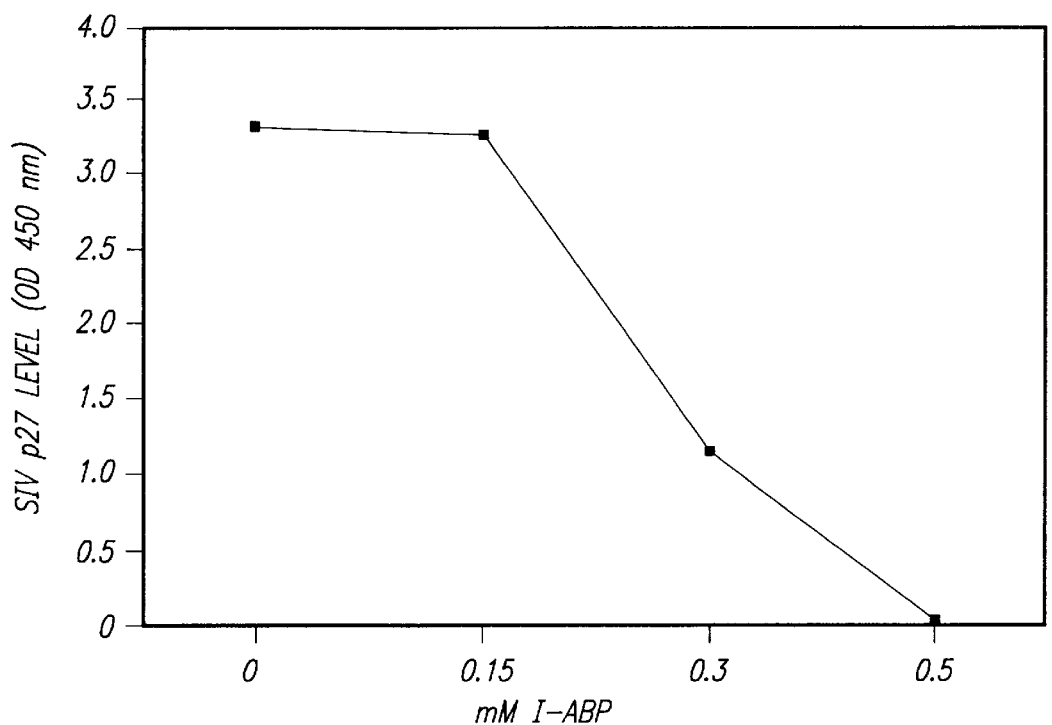
FIG. 8 shows the effect of IABP on SIVmac239 replication. CEM ×174 cells ($3\times10^5$/ml) were infected with SIVmac239 on day 0 and incubated for 3 days (37° C., 5% $CO_2$) before treatment with IABP (0–0.5 mM). The cultures were incubated for an additional 4 days before being replenished with fresh CEM ×174 cells ($3\times10^5$/ml) and IABP. On day 10 the levels of free virus in the supernatants of the cultures were assessed using the SIV p27 core antigen assay (Coulter Corp). The absorbance was measured at 450 nm.

The subject invention also provides for methods of decreasing the titer of infectious viruses, particularly retroviruses (including the retrovirus HIV-1) in biological materials by inactivating the viruses with one or a plurality of synergistic compositions (FIG. 8). Viruses may be inactivated by contact between a synergistic composition of interest and the virus. The term "decreasing" includes the complete elimination of all the infectious viruses of interest, as well as a diminution in the titer of the infectious viruses. It is of particular interest to decrease the number of infectious viruses in biological material that is to be introduced into a living organism so as to reduce the possibility for infection. It is also of interest to decrease the titer of infectious viruses that might be present in or on non-biological materials that come into contact with living organisms. Such non-biological materials include surgical instruments, dental instruments, hypodermic needles, public sanitary facilities, and the like. Inactivation of HIV virions occurs by direct acting C-nitroso pADPRT CCHC-oxidizing ligands only—not by C-nitro precursors.

The subject methods inactivate viruses by employing the step of contacting an effective amount of one or a plurality of synergistic compositions to the biological or non-biological material of interest. A preferred embodiment of the subject method is decreasing the concentration of infectious virus in blood. Another preferred embodiment of the subject invention is the inactivation of AZT resistant viruses and retroviruses, particularly HIV and SIV.

The subject invention also provides for methods of inducing apoptosis in a tumor cell by administering one or a plurality of synergistic compositions to a cell culture or a mammalian host having one or a plurality of tumors.

The invention having been described, the following examples are offered to illustrate the subject invention by way of illustration, not by way of limitation.

EXAMPLES

I. Syntheses

A. 6-Nitroso-1,2-Benzopyrone

An example of a method for the preparation of 6-nitroso-1,2-benzopyrone is provided as follows:

To a stirred solution of 6-amino-1,2-benzopyrone hydrochloride (4.00 g, 20 mmol) in water (40 ml) at 22° C. was added a solution of sodium tungstate (5.93 g, 20 mmol) in water (20 ml) followed by 30% aqueous hydrogen peroxide (5 ml) and stirring was continued for 1.5 hours. The oxidation product was extracted from the green-colored mixture with two 100 ml volumes of ethyl acetate, the combined extracts washed with 0.1N HCl (50 ml) and then water (100 ml). The ethyl acetate was removed by rotary evaporation and the residue recrystallized from warm ethanol (250 ml).

Analysis of Reaction Product

The green crystals obtained from the recrystallization step (1.48 g, 42% yield) displayed light absorption at 750 nm characteristic of monomeric arylnitroso compounds. Mass spectrum: m/z (relative intensity): 175 ($M^+$, 100), 161 (16.88), 145 (33.77), 133 (10.38), 117 (56.09), 89 (79.71), 63 (57.13). High resolution data for the $M^+$ peak: calculated for $C_9H_5NO$; 175.0268; found: 175.0271 (deviation=1.1 ppm). $^1$H-NMR ($CDCl_3$, 300 MHz) δ (ppm) from TMS: doublet (6.572 and 6.604) H-4 split by H-3; doublet (7.472 and 7.501) H-8 split by H-7; doublet of doublets (7.860/7.866 and 7.889/7.798) H-7 split by H-8 and finely split by H-5; doublet (7.910 and 7.942) H-3 split by H-4; doublet (8.308 and 8.315) H-5 finely split by H-7. UV/VIS spectrum in ethanol, λ max (ε): 750 nm (46), 316 nm ($8.96 \times 10^3$), 274 nm ($2.24 \times 10^4$). Melting Point: The compound polymerizes above 160° C., blackens and melts in the range of 325°–340° C.

This nitroso-compound may also be prepared by reacting 6-amino-1,2-benzopyrone (as the free base) with 3-chloroperoxybenzoic acid in ethyl acetate or halocarbon solvents.

B. 3-nitrosobenzamide, 2-nitrosobenzamide and 4-nitrosobenzamide

To a stirred solution of 3-aminobenzamide (Aldrich Chemical Co.) (0.476 g, 3.50 mmol) in ethyl acetate (50 ml) at ambient temperature was added 1.208 g of 3-chloroperoxybenzoic acid (commercial grade, 50–60% purity, Aldrich), whereupon the solution turned green. After 10 minutes the mixture was extracted with 0.14M aqueous sodium bicarbonate (58 ml), washed with three successive 40-ml portions of water, dried over sodium sulfate, then reduced in volume to 20 mL by rotary evaporation and placed in the freezer (−20° C.), whereupon the product slowly deposited as a light yellow solid during a period of 72 hours (0.180 g, 34% yield).

The 2-nitrosobenzamide and 4-nitrosobenzamide isomers may be similarly prepared by oxidizing 2-aminobenzamide and 4-aminobenzamide, respectively.

Analysis of Reaction Product

Melting point: The substance darkens above 135° C., softens and apparently polymerizes in the range 150°–160° C., and melts at 240°–250° C. (with decomposition). In solution the compound is green-blue. Mass spectrum: m/z (relative intensity): 150 ($M^+$, 100), 136 (10.9), 120 (77.2), 103 (31.6), 92 (46.5), 85 (22.8), 71 (33.3). High resolution data for the $M^+$ peak: calculated for $C_7H_6N_2O_2$: 150.04292 found: 150.042900 (deviation=0.2 ppm). NMR spectrum: $^1$H-NMR (DMSO-$d_6$, 300 MHz) δ (ppm) from TMS: broad singlet (7.737) N-H; t (7.824, 7.850, 7.875) H-5 split by H-4 and H-6; d (8.059 and 8.086) H-6 split by H-5; d (8.357 and 8.383) H-4 split by H-5; s (8.472) H-2. The singlet at 7.737 corresponds to 1 proton; the second N-H proton, spectrally non-equivalent in this compound, is overlaid by the doublet of H-4. This doublet integrates to 2 protons and can be resolved by addition of $D_2O$ to the DMSO solution. UV-VIS absorption spectrum in absolute ethanol, λ max (ε): 750 nm (37.6), 304 nm ($5.35 \times 10^3$) and 218 nm ($1.50 \times 10^4$). An absorption maximum at 750 nm is characteristic of monomeric arylnitroso compounds.

In another embodiment, 3-nitrosobenzamide is synthesized by dissolving 3-aminobenzamide (5.0 g) in N,N-dimethylformamide (DMF) solvent (25 ml) and then chilled in an ice bath. 3-Chloroperoxybenzoic acid (2.1 equivalents) is also dissolved in DMF solvent (25 ml) in a 250-ml flask equipped with a stirrer and thermometer and, as needed, an ice bath. This solution is chilled to 0°–5° C., the ice bath is removed, and to it, with stirring, is added all at once the chilled 3-aminobenzamide solution. The mixture immediately becomes a transparent brown color, but within 0.5 minute turns to a deep green, and within 1.0 minute the temperature rises to 70° C., at which time the ice bath is reapplied to the reaction flask whereupon the temperature begins to fall, and is allowed to fall to 25° C., and stirring is continued for a total of 5 minutes. Some precipitation occurs (3,3'-azoxybenzamide side-product), thereafter the mixture is chilled to 5° C. for 10 minutes. The chilled mixture is filtered (suction) to remove the azoxy precipitate, and the green filtrate is poured into chilled (5°–10° C.) and stirred aqueous 0.40M $Na_2CO_3$ (200 ml), resulting in a light green suspension, and the suspension is stirred for an additional 10 minutes at 5°–10° C. to assure maximal product precipitation. Note that the pH of the suspension is about 8.5, which assures that 3-chlorobenzoic acid is retained in the aqueous solution as the sodium salt. The precipitate is then collected on a suction funnel and rinsed with deionized water (100 ml). This material, which is 3-NOBA (mostly as the tan dimer) containing residual 3,3'-azoxybenzamide side-product impurity, is then transferred, while damp, to a suitable flask and to it is added 50% aqueous acetic acid (200 ml). The mixture is warmed to 65°–70° C. to dissolve the dimer into the soluble monomeric 3-NOBA (green) and stirred for 5 minutes at 65° C. The azoxy impurity (yellow) is poorly soluble and remains undissolved, The warm mixture is filtered (gravity) to give a clear green filtrate, which is allowed to cool. It is then chilled and placed in the refrigerator freezer (−20° C.) overnight to allow the 3-NOBA to redeposit as the light tan solid dimer. On the following day the solid product is collected on a suction filter, rinsed with fresh solvent, and the product cake is then dried by vacuum under mild warming for several hours. One typically obtains 2.24 g of dry 3-NOBA containing a trace of the azoxy impurity. The product is recrystallized by dissolving it again in 50% aqueous acetic acid (120 ml) and allowing to redeposit overnight in the freezer. After collection, rinsing and drying in vacuo, the weight is 2.08 g (37% overall yield). TLC shows the material is 3-NOBA with a trace of the azoxy impurity.

C. 4-Iodo-3-Nitrobenzamide

In a 100-mL flask equipped with a magnetic stirrer, thermometer and ice bath, a stirred solution of 4-Iodo-3-nitrobenzoic acid (1025 mg, 3.50 mMoles) (Chemica Alta Ltd., Edmonton, Alberta, Canada) in N,N-dimethylformamide (10 mL) is cooled to 10° C., and then thionyl chloride (0.76 mL, 10.5 mMoles) is added to it. There is no exothermicity, the ice bath is removed, and the solution is allowed to warm to ambient temperature, and stirring is continued for a total of 1 hour. Then the solution is poured into chilled, concentrated ammonium hydroxide (20 mL), resulting in a dark yellow mixture, which is stirred for 5 minutes. Then chilled deionized water (50 mL) is added, causing precipitation of the light yellow product. After allowing the precipitation mixture to stand chilled on ice for 10 minutes, the precipitate is collected on a suction filter, rinsed with cold water, and then dried by vacuum pumping. The resultant crude product (500.4 mg) is then re-crystallized by dissolving it in acetonitrile (7.0 mL) heated to about 65° C., followed by cooling and allowing the solution to stand in the refrigerator overnight. The yellow crystals are collected, rinsed with chilled solvent and dried by vacuum pumping, to give 415.2 mg (40.5% yield) of 4-Iodo-3-nitrobenzamide, m.p. 152°–155° C.

$^1$H NMR spectrum, in DMSO-$d_6$ δ (ppm) values relative to TMS): broad singlet (7.67) due to one nonequivalent proton of the amido $NH_2$ group; doublet of doublets (7.84, 7.85 and 7.86, 7.87) due to H-5 split by H-6 and finely split by H-2; doublet (8.22, 8.24) due to H-6 split by H-5; broad singlet centered near 8.22, overlapping the signal of H-6, due to the second nonequivalent proton of the amido $NH_2$ group; doublet (8.35, 8.36) due to H-2 finely split by H-5. At higher NMR field signals due to adventitious water (2.5 ppm), deuterated-DMSO impurity protons (3.3 ppm) and crystallization solvent acetonitrile (single at 2.07 ppm) are observed. Integration of the acetonitrile signal indicates approximately one molecule of acetonitrile per 3 molecules of 4-iodo-3-nitrobenzamide.

UV absorption spectrum in absolute ethanol, λ max (ε): 308 nm (1.59×10³), 242 nm (1.31×10⁴), 208 nm (1.45×10⁴)

Elemental analysis (Schwarzkopf Microanalytical Laboratory): Calculated for $C_7H_5N_2O_3I$: C, 28.79%; H, 1.72; I, 43.46; N, 9.59. Found: C, 29.63; H, 1.72; I, 41.47; N, 9.99. Deviations from calculated are believed to be due to the presence of acetonitrile (crystallization solvent) as detected in the NMR spectrum. High resolution EI mass spectrum: calculated for $C_7H_5N_2O_3I$: 291.9345; Found: M⁺ (m/z) 291.9349 (deviation=−1.4 ppm).

D. 4-Iodo-3-Nitrosobenzamide

The method of synthesis of INOBA differs from that for 4-iodo-3-nitrosobenzamide in that a different oxidant is required. In a procedure favoring oxidation to the nitroso state, each of 20 test-tubes (13×100 mm) was charged with 5.2 mg (0.020 mmol) of $INH_2BA$ (synthetic), Mendeleyev et al. (1994), see also Example I.J., and 0.100 ml of absolute EtOH. Each tube was heated briefly to dissolve the amino compound, followed immediately by $H_2O$ (0.400 ml) and then peracetic acid reagent (0.400 ml, 32% in dilute acetic acid) added at a fast drip during 10 sec. After 2 min., ethyl acetate (2.0 ml) and $H_2O$ (2.0 ml) were added, the mixture vortexed, and then stored on ice while the other tubes were identically processed. The upper (ethyl acetate) layers were pooled, the solution concentrated (rotary evaporation) to 4 ml, $H_2O$ added until turbid, and placed at 2° C. for 18 h. The product deposited as a light tan solid. Yield: 35.3 mg (32%), m.p. 174°–176° C. (decomp). High resolution EIMS: calculated for $C_7H_5N_2O_2I$: 275.9396; found M⁺ (m/z): 275.9399 (deviation=−0.3 ppm). $^1$H NMR (DMSO-$d_6$) δ (ppm): 6.65 (1H, d, J=2.2 Hz), 7.60 (1H,s) 8.02 (1H, dd, J=81 Hz, J=2.2 Hz), 8.18 (1H,s) 8.50 (1H, d, J=2.2 Hz). UV: max 370, 252, 226 nm and shoulders at 315, 293 nm. Vis: max 750 nm.

E. Nitroso-1(2H)-isoquinolinones (a mixture of 5-nitroso and 7-nitroso isomers)

1-(2H)-Isoquinolinone (isocarbostyril) (Aldrich) was nitrated using a general method for isoquinolinone compounds. C. G. LeFevre and R. J. W. LeFevre, *J. Chem. Soc.* 1470 (1935. The nitration product (a mixture of the 5-nitro and 7-nitro isomers, as assigned by Y. Kawazoe and Y. Yoshioka, *Chem Pharm. Bull.* (Tokyo) 16:715–720 (1968), although one of the isomers could be the 8-nitro isomer) was then reduced to the corresponding amino-1(2H)-isoquinolinones using a combination of potassium borohydride and palladium-on-carbon catalyst in aqueous methanol. To the resultant amino-1(2H)-isoquinolinones (as free bases) (0.560 g. 3.50 mmol) in ethyl acetate (175 mL) at 30° C. was added 1.208 g of 3-chloroperoxybenzoic acid (Aldrich). The mixture became cloudy and after 20 minutes it was filtered, extracted with 0.14M sodium bicarbonate (58 mL), washed with two 50-mL portions of water, and dried over sodium sulfate. The volume of the solution was reduced to 50 mL by rotary evaporation and then placed in the freezer (−20° C.), whereupon an orange solid product was deposited (0.102 g).

Analysis of Reaction Product

Melting point: substance darkens above 175° C., softens, blackens and apparently polymerizes above 195° C., and finally melts in the range 310°–335° C. NMR analysis: $^1$H-NMR (DMSO-$d_6$/$D_2O$, 300 MH$_z$) δ (ppm) from TMS: m (6.723, 6.741, 6.752); m (7.511, 7.518, 7.533, 7.539, 7.547, 7.559, 7.577, 7.585); m (7.663, 7.674, 7.686, 7.698, 7.707); d (7.818, 7,846). In the absence of $D_2O$, the compound also displays a broad singlet at 11.90 ppm. The isomeric components were analytically resolved by thin-layer chromatography (silica gel plates, ethyl acetate solvent), giving two bands, $R_f$ 0.82 and $R_f$ 9.72. Mass spectrum for $R_f$ 0.82: m/z (relative intensity): 174 (M$^+$, 100), 160 (26.8), 144 (93.0), 117 (90.8), 97 (21.9), 89 (96.1), 71 (24.1). High resolution data for the M$^+$ peak: calculated for $C_9H_6N_2O_2$: 174.042928; found: 174.043200 (deviation=–0.3 ppm). For the component having $R_f$ 0.72, M$^+$, calculated for $C_9H_6N_2O_2$: 174.042928; Found: 174.043200 (devation=–1.6 ppm). These data confirm that the compounds are mono-nitroso isomers.

F. Iodo-Nitro Substituted Estrones

The method of total estrone synthesis of Bachman et al., J. Amer. Chem. Soc. 64:974 (1942) is used for the synthesis of iodo-nitro substituted estrones. These products are compounds of the following formula:

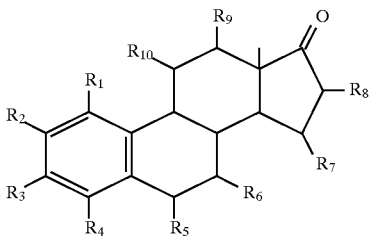

wherein, $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the ten , substituents are hydrogen, and wherein at least one of the ten $R_1$, $R_2$, $R_3$, $R_4$, $R_5$, $R_6$, $R_7$, $R_8$, $R_9$ and $R_{10}$ substituents is nitroso or nitro.

G. Iodo-Nitro Substituted Equilenins

The method of Bachman et al., J. Amer. Chem. Soc. 61: 974 (1939) is used for the synthesis of iodo-nitro substituted equilenins. These products are compounds of the following formula:

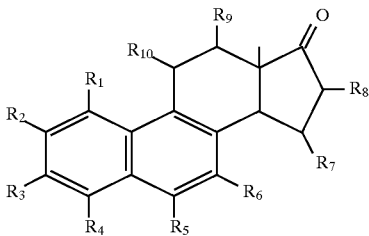

wherein $R_1$, $R_2$, $R_3$, $R_4$, $R_5$, $R_6$, $R_7$, $R_8$, $R_9$ and $R_{10}$ are, independent of one another, selected from the group consisting of hydrogen, hydroxy, nitroso, nitro, iodo ($C_1$–$C_6$) alkyl, ($C_1$–$C_6$ alkoxy, ($C_3$–$C_7$) cycloalkyl, and phenyl and pharmaceutically acceptable salts thereof, wherein at least three of the nine $R_1$, $R_2$, $R_3$, $R_4$, $R_5$, $R_6$, $R_7$, $R_8$, $R_9$ substituents are hydrogen, and wherein at least one of the ten $R_1$, $R_2$, $R_3$, $R_4$, $R_5$, $R_6$, $R_7$, $R_8$, $R_9$ and $R_{10}$ substituents are nitroso or nitro.

H. 2-Iodo-5-Nitroso-Benzamide

The synthesis of 2-iodo-5-nitroso-benzamide can be performed similarly to the synthesis of 4-iodo-3-nitroso-benzamide, described above, using 2-iodo-5-nitro benzoic acid (Chemica Alta Ltd., Edmonton, Alberta, Canada) as the starting material.

I. 2-Iodo-5-Nitro-Benzamide 2-iodo-5-nitro-benzamide was synthesized by the method previously described for 4-iodo-5-nitro-benzamide using 2-iodo-5-nitro benzoic acid (Chemica Alta Ltd., Edmonton, Alberta, Canada) as the starting material.

$^1$H NMR Spectrum, in DMSO-$d_6$ δ (ppm) values relative to TMS: 7.742 (1H, singlet); 7.943 (1H, doublet of doublts, J=8.26 Hz, J=2.58 Hz); 8.034 (1H, singlet), 8.064 (1H, doublet, J=2.94 Hz); and 8.191 (1H, doublet, J=8.46 Hz).

Mass Spectrum:

Low resolution electron impact spectrum (m/z): 292 (M$^+$), 276, 230, 202, 165, 127, 91, 75, 63. High resolution measurement of M$^+$: Calculated for $C_7H_5IN_2O_3$: 291.934494; found: 291.934149 (deviation=1.2 ppm).

Melting Point: melting point 230°–233° C.

J. 4-Iodo-3-Aminobenzamide

INO$_2$BA (730 mg, 2.50 mmol) was dissolved in warm EtOH (25 mL) to which was then added $H_2O$ (25 mL) at 24° C. followed by 1M sodium dithionite (50 mL, freshly prepared in 0.05M sodium bicarbonate). After 15 min. the product was extracted into ethyl acetate which was then removed by rotary evaporation, and the residue crystallized from hot $H_2O$ (40 mL). Yield: 139 mg (21%). This amino compound does not form a hydrochloride.

Microanalysis: Calculated for $C_7H_7IN_2O$: C, 32.08; H, 2.69; I, 48.43; N, 10.69. Found: C, 31.57; H, 2.37; I, 48.70; N, 10.02.

$^1$H NMR Spectrum, in DMSO-$d_6$, δ (ppm): 5.30 (2H, multiplet, amino protons), 6.79 (1H, dd, J=8.2 Hz, J=1.9 Hz), 7.17 (1H, s), 7.23 (1H, d, J=1.9 Hz), 7.60 (1H, d, J=8.0 Hz), 7.75 (1H, s).

UV absorption spectrum, λ max (ε): 322, 230 nm and shoulders at 252, 220 nm.

Melting point: melting point 175°–180° C. (decomp.).

K. 6-Amino-1,2-benzopyrone

The synthesis of 6-amino-1,2-benzopyrone is reported in Cole et al., Biochem Biophys. Res. Commun. 180:504–514 (1991).

L. 5-Iodo-6-Amino-1,2-Benzopyrone

The synthesis of 5-iodo-6-amino-1,2-Benzopyrone is reported in Cole et al., Biochem Biophys. Res. Commun. 180:504–514 (1991).

M. Further Examples

Compounds of formulae IV–IX are synthesized in a manner similar to Examples I.F. and I.G., above.

In a preferred mode compounds I–IX are synthesized with an iodo group adjacent to a nitro or nitroso group. In a more preferred mode, compounds I–IX are synthesized with an iodo group adjacent to a nitro group.

In an even more preferred mode compounds of formulae I and II are selected from the group consisting of 4-iodo-3-nitro-benzamide, 2-iodo-5-nitro-benzamide and 5-iodo-6-nitro-1,2-benzopyrone.

II. $I_{50}$ and $LD_{100}$ Values for Nitroso- and Nitro-Compounds in (A) Mammary Cancer Cells (monolayer cultures) and in (B) L-1210 Murine Leukemia Cells (suspension culture).

The effect of nitroso- and nitro-compounds in mammary cancer cells and in murine leukemia cells is shown in Table 1.

TABLE 1

| (A) | (Namomoles/cm × 10⁴ cells) | | | | | |
|---|---|---|---|---|---|---|
| | MDA 468 | | MCF-7 | | BT 474 | |
| Cell line: | I 50 | LD100 | I 50 | LD100 | I 50 | LD100 |
| NOBA | | | | | | |
| INO₂BA | 85 | 195 | 100 | 250 | 90 | 200 |
| 4-iodo-3-NO₂-benzoic acid | 180 | n.d. | 145 | n.d. | 160 | n.d. |
| INO₂BP | 260 | n.d. | 250 | n.d. | 260 | n.d. |

Seeding was at $2 \times 10^4$ or $0.8 \times 10^4$ cells/cm², drugs were added 6–18 hours after seeding, and drug exposure time was 24–48 hours.

| (B) | L 1210 Cells (nanomoles/10⁵ cells) | |
|---|---|---|
| | I 50 | LD100 |
| NOBA | 7.5 | 15 |
| NO₂BA | 16 | 32 |
| 4-Iodo-3-NO₂-benzoic acid | 16 | 32 |
| NO₂BP | 35 | 80 |

Cells were seeded at $5 \times 10^4$ to $2 \times 10^5$/ml; drugs were added at the time of seeding; drug exposure was for 18 hours.

III. Comparison of pADPRT Inactivation and pADPRT Zinc Content by NOBA and INOBA NOBA and INOBA were assayed for their respective effects on pADPRT enzyme inactivation and pADPRT zinc content according to the methods described in Buki et al., *FEBS Lett.* 290:181–185 (1991) at pH 7.0. pADPRT inactivation was performed in 20-μl volumes of buffer containing 50 mM Hepes (pH 7.4), 100 mM KCl, 0.5 mM EDTA, pADPRT (0.4 μg/μl) and different concentrations of inactivators. Inactivators were serially diluted in the above buffer from a 20 mM stock solution in DMF. The DMF concentration (2.5%) was kept constant in the inactivation mixes. After 2 hr at 25° C., aliquots (3 μl) were removed for assay of enzyme activity in a volume of assay mix (200 μl) which the inactivators were dilute enough not to act as inhibitors. The assay mix consisted of 100 mM Tris (pH 7.7), 14 mM 2-mercaptoethanol, 0.1 mM [$^{32}$P]-NAD⁺, 0.2 mg/ml coDNA and 0.1 mg/ml histones. The result of the pADPRT assays are shown in FIG. 1. The incorporated $^{32}$P, proportional to enzyme activity, is plotted as percent of the untreated sample. The effect of NOBA and INOBA on the zinc content of pADPRT is shown in FIG. 2. In these experiments $^{65}$Zn$^{2+}$-labeled pADPRT was used.

The Zn$^{2+}$ content of pADPRT (FIG. 2A, upper panel) was determined as follows: two parallels of aliquots (4 μl) were pipetted into 500 μl of ice-cold washing solution (50 mM Tris, pH 7.7, 10 mM 2-mercaptoethanol and 0.5 mM EDTA) then filtered onto GF/C disks presoaked in washing solution (cold), quickly washed 4 times with 1 ml of ice-cold washing solution, dried, and the radioactivity determined. The protein-bound $^{65}$Zn$^{2+}$ is shown as percent of the untreated sample. Enzyme assays (FIG. 2A, lower panel) were performed as in FIG. 1.

For the release of Zn$^{2+}$ from transblotted pADPRT, the enzyme (3 μg per lane) was separated on SDS-PAGE, transblotted onto a nitrocellulose membrane, and renatured in the presence of $^{65}$ZnCl₂. The Zn$^{2+}$-loaded transblot was cut into strips and incubated with 2 ml of 50 mM Hepes/NaOH (pH 7.0) and 0.5 mM EDTA containing different concentrations of either NOBA or INOBA as indicated, for 2 hr. at 25° C. After incubation, 1 ml of the supernatant was counted for radioactivity, and the strips were washed 3 times with 2 ml of 50 mM Tris-HCL pH 7.4), 0.5 mM EDTA and 10 Mm 2-mercaptoethanol, and then dried and exposed to X-ray film. The intensity of the autoradiographic spots was quantitated by a scanner. The results are shown in FIG. 2B.

IV. Effectiveness of 4-(halogen)-3-nitro-benzamide compounds as tested with human T-lymphoblastoid leukemia cell lines in culture.

| | I$_{50}$ | LD$_{100}$ |
|---|---|---|
| 4-iodo-3-nitro-benzamide | 70 | 190 |
| 4-fluoro-3-nitro-benzamide | 120 | 280 |
| 4-chloro-3-nitro-benzamide | 130 | 300 |
| 4-bromo-3-nitro-benzamide | 120 | 290 |

Cells (MT-2 cells, or, in case of 3-fluoro-4-nitro-benzamide, CEM-4 cells) were seeded at a density of $0.1 \times 10^5$/ml; the drugs were added at the time of seeding. The cultures were incubated at 37° C. in a 5% CO₂ atmosphere and the cells numbers were monitored by hemacytometer counting in 24 hr intervals. "I$_{50}$" values (left column) represent the concentrations estimated to decrease cell viability to 50% of control; "LD$_{100}$" values (right) are concentrations that achieved zero viability after 48 hours of incubation.

V. Comparison of Cytostatic and Cytocidal Activity of 4-Iodo-3-Nitrobenzamide and 2-Iodo-5-Nitrobenzamide The cytostatic and cytocidal activity of 4-iodo-3-nitrobenzamide and 2-iodo-5-nitrobenzamide are shown below:

| | Cytstatic Effect I$_{50}$ (E ras cells) | Cytocidal Effect I$_{50}$ (with 0.8 mM BSO) |
|---|---|---|
| 4-iodo-3-nitrobenzamide | 60 μM | 4 μM |
| 2-iodo-5-nitrobenzamide | 12 μM | 2 μM |

Each value is the average of three trials. Each trial deviated from the average by no more than twenty percent. The 2-iodo-5-nitrobenzamide isomer is the more effective of the two isomers tested at inducing cytostatic and cytocidal effects. Another isomer of the iodo-nitro-benzamide series, 2-iodo-4-nitrobenzamide had no effect at the concentrations given above.

VI. Metabolic Conversion of INO₂BA to INH₂BA

It is known that GSH adds to aromatic nitroso compounds to form labile adducts (semimercaptals) one of whose reaction pathways is molecular rearrangement (oxygen atom migration) to yield sulfinamides that hydrolyse to the corresponding amines plus glutathione sulfinic acid (Equation 1). Eyer et al., *Chem. Biol. Interactions* 24:227–235 (1979); Umemoto et al., *Chem. Biol. Interactions* 68: 57–69 (1988); Ellis et al., *Chem. Biol. Interactions* 82:151–163 (1992).

Equation 1

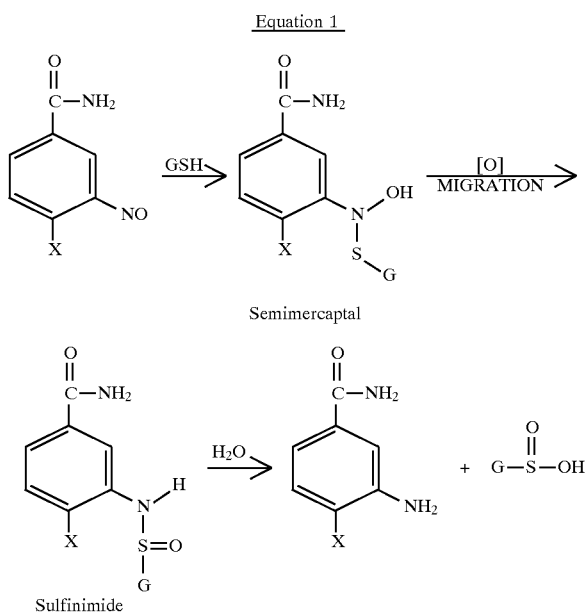

Where X-H or I;
GSH is glutathione (γ-L-glutamyl-L-cysteinylglycine tripeptide);
G—S—denotes the glutathion-S-yl group in the semimercaptal; and
G—S(O)—denotes the glutathione sulfinyl group in the oxidized species The cell metabolites of INO$_2$BA metabolism were identified. A suspension of 855-2 cells (6), 150×10$^6$ cells in ml of RPMI-1640 medium, was dosed with INO$_2$BA to a concentration of 120 μM, incubated at 37° C. for 18 hr, and then freeze-dried, extracted 3 times with EtOH (10 ml each time) for 30 min and centrifuged. The extract was rotary evaporated to dryness, redissolved in EtOH (3.0 ml), microfuged to remove small particles, and aliquots (200 μl) injected into HPLC. In control experiments, instead of incubating the drug-dosed cell suspension it was immediately frozen, freeze-dried and extracted. HPLC analyses were performed essentially as reported earlier, except the pH of the buffers was 4.3. Buki et al., *FEBS Lett*. 290:181–185 (1991). Upon sample injection the gradient started from 100%A to 100%B in 30 min, to 50%B/50%C in 15 min, to 100%C in 3 min. Retention times of synthetic standards were: 4-iodo-3-hydroxylaminobenzamide 18.7 min; 4-iodo-3-aminobenzamide ("INH$_2$BA") 24.7 min; INO$_2$BA 34.5 min; INOBA 36.5 min and 6,6'-diiodo-3,3'-dicarbamoylazoxybenzene 46.9 min.

A slow but apparently steady reduction of the nitro to the amino end-product occurred at a rate of 2.2±0.2% per 18 hrs of cell incubation at 37° C. Apart from as yet unidentified trace metabolites the only identified metabolite was INH$_2$BA (see Equation 1, where X=I). The removal of GSH by BSO augments the rate of accumulation of INOBA from INO$_2$BA by decreasing the rate of removal by GSH, as deduced from the pathway shown in Equation 1.

VII. Cytocidal Effect of NOBA and INO$_2$BA in Combination With Ascorbate

Because of the in vitro reactivity of the nitroso group of INOBA with both ascorbate and GSH, the apoptosis-inducing effect of NOBA with the action of the prodrug INO$_2$BA in the presence of ascorbate, added simultaneously with both drugs was compared. As shown in Table 2, 160 μM ascorbate, which by itself had no effect on AA-2 leukemia cells, completely protected against the apoptosis-inducing action of NOBA, but did not prevent apoptosis by INO$_2$BA after 18 hr of drug exposure. These results are readily explained by the rapid chemical reduction of the nitroso group in NOBA to the hydroxylamine, and the rapid cellular oxidation of ascorbate to its oxidized form. Since the generation of INOBA from its prodrug is slow and steady, it would be expected that the apoptosis-inducing capacity of the prodrug is sustained for the entire duration of the incubation (18 hr) whereas the rapid oxidative removal of the ascorbate takes place in minutes, thus its protective effect is of short duration only. However these results predict that a chemotherapeutic efficiency of the prodrug would be much greater in species that do not synthesize ascorbate.

TABLE 2

Cytocidal Effect of NCBA and INO$_2$BA in combination with Ascorbate

| | cell number (×10$^6$/ml) | |
|---|---|---|
| | Day 1 | Day 2 |
| Control | 0.51 | 0.90 |
| Ascorbate (160 μM) | 0.48 | 0.90 |
| NOBA (32 μM) | 0.29 | 0.37 (50% dead) |
| NOBA + Ascorbate | 0.57 | 0.91 |
| INO$_2$BA (16 μM) | 0.25 | 0.45 (40% dead) |
| INO$_2$BA + Ascorbate | 0.27 | 0.50 (40% dead) |

AA-2 cells were seeded at a density of 0.2×10$^6$ cells/ml. Drugs and/or sodium ascorbate were added at the time of seeding, and cells were counted by hemacytometer after incubation (37° C., 5% CO$^2$) for 18 hr (Day 1) and for 42 hr (Day 2). Viability was evaluated by Trypan Blue exclusion. Assays were performed in triplicates and deviation from averages did not exceed ±15%.

Figure 3:
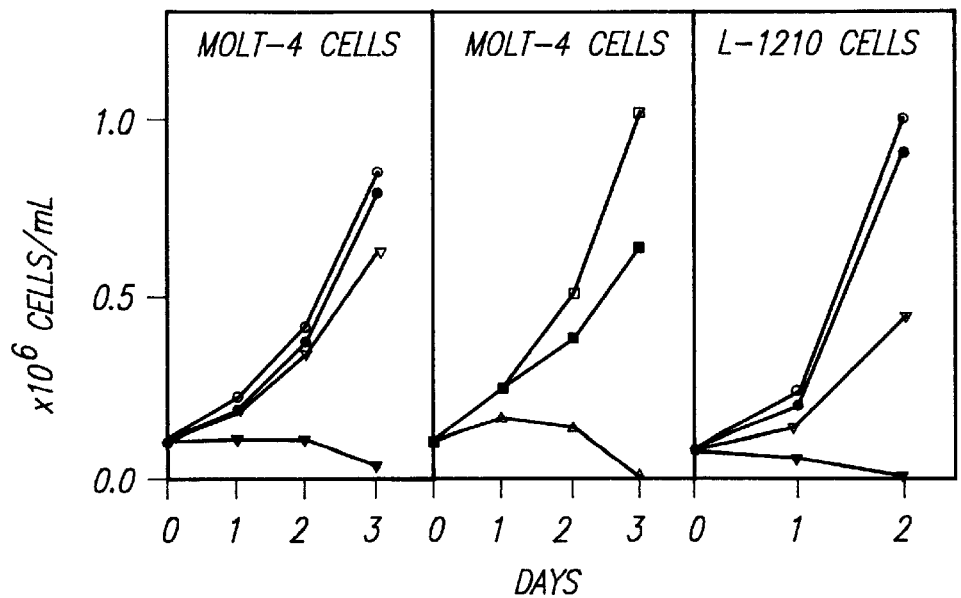
FIG. 3 shows the time course of cell killings by 4-iodo-3-nitrobenzoic acid, INO$_2$BA and NOBA, respectively, alone and in combination with BSO. Molt 4-cells were seeded at a density of 0.05×10$^6$ cell/ml in the recommended growth medium in the absence or the presence of drugs as indicated. Cells were incubated at 37° C. in a 5% CO$_2$ atmosphere and proliferation was monitored in 14 hr. by cell counting in a hemacytometer. ○, untreated control; ●, treated with 4 μM 4-iodo-3-nitrobenzoic acid; ▽, treated with 1 mM BSO; ▼, treated with 4 μM-iodo-3-nitrobenzoic acid and 1 mM BSO; □, treated with 4 μM 4-INO$_2$BA; ■, treated with 1 mM BSO; ▽, treated with 4 μM INO$_2$BA and 1 mM BSO. L-1210 cells were seeded at a density of 0.05×10$^6$ cells/ml either from untreated stock suspensions or from 24-hr. pretreated (0.2×10$^6$ cells/ml) suspensions. ○, untreated control; ●, treated with 5 μM NOBA; ▽, treated with 1 mM BSO; ▼, 24-hr pretreatment with 1 mM BSO then treated with 4 μM NOBA.

VIII. Synergistic Cytotoxic Effects of 4-Iodo-3-Nitrobenzoic Acid, INO$_2$BA and NOBA, Respectively, in Combination with BSO A time course of the cell killings by 4-iodo-3-nitrobenzoic acid, INO$_2$BA and NOBA, each alone and in combination with BSO was obtained. Molt-4 cells were seeded at a density of 0.05×10$^6$ cells/ml in the recommended growth medium in the absence or presence of drugs as indicated in FIG. 3. Drugs were added to the wells immediately after seeding from 10–40 mM stock solution in DMSO. BSO was added from a 100 mM aqueous stock solution. Cells were incubated at 37° C. in a 5% CO$_2$ atmosphere and proliferation was monitored in 14 hours by cell counting in a hemacytometer. The results of the experiment are shown in FIG. 3.

As is apparent from FIG. 3, 4-iodo-3-nitrobenzoic acid, INO$_2$BA and NOBA had no significant effect on the cell proliferation of either Molt-4 cells or L-1210 cells over a 2–3 day period. BSO alone also had no significant effect on cell proliferation during this period. BSO in combination with each of the drugs showed rapid synergistic cytocidal effects in both Molt-4 and L-1210 cells as followed for 2–3 days.

Inasmuch as we find that some malignant cell types contain pADPRT which is not auto-poly-ADP-ribosylated in the intact cell, Cole et at., *Biochem Biophys. Res. Commun* 180:504 (1991), a structural analog of INOBA not containing the carboxamide group, 4-iodo-3-nitrosobenzoic acid (via its nitro precursor), would not be expected to bind to pADPRT, because only the carboxamide group effectively binds at the nicotinamide site. Althaus and Richter, *ADP-*

*Ribosylation of Proteins: Enzymology and Biological Significance*, Springer-Verlag, Berlin (1987). The majority of tumor cells respond to the benzamide-containing prodrug much more readily than to the carboxylic acid. That reduction of the prodrug to its nitroso species is essential for induction of apoptosis is evident from the large activating effect of BSO, which by diminishing cellular GSH decreases the rate at which GSH chemically reduces, and thus inactivates, the nitroso molecules generated.

IX. Synergistic Effect of $INO_2BA$ in Combination with BSO on Cytotoxicity of Various Cancer Cell Lines The role of cellular GSH was determined by the simultaneous addition of $INO_2BA$ and BSO (an inhibitor of GSH biosynthesis, Meister, *Pharmacology and Therapeutics* 51:155–194 (1991), which at the concentrations applied diminished cellular GSH levels below 5–10% of controls.) The results are tabulated below in Table 3.

TABLE 3

Synergistic effect of DL-buthionine sulfoximine (BSO) on cytotoxicity of $INO_2BA$ in various cancer cell lines

| No. | Cell Line | $I_{50}$ ($\mu$M) $INO_2BA$ | $I_{50}$ ($\mu$M) $INO_2BA$ + BSO | $LD_{100}$ ($\mu$M) $INO_2BA$ | $LD_{100}$ ($\mu$M) $INO_2BA$ + BSO |
|---|---|---|---|---|---|
| 1 | MDA-468 | 80 | 15 | 180 | 40 |
| 2 | MCF-7 | 100 | 16 | 200 | 30 |
| 3 | MCF-7-B-ADR | 90 | 16 | 220 | 45 |
| 4 | Du 145 | 120 | 20 | 250 | 50 |
| 5 | HT 144 | 100 | 15 | 200 | 35 |
| 6 | Hep-G2 | 120 | 20 | 200 | 45 |
| 7 | PC-12 | 60 | 16 | 120 | 50 |
| 8 | L 1210 | 128 | 20 | 256 | 64 |
| 9 | CEM-4 | 80 | 15 | 196 | 32 |
| 10 | HL 60 | 70 | 8 | 125 | 16 |
| 11 | Molt-4 | 70 | 15 | 196 | 32 |
| 12 | U 937 | 65 | 8 | 150 | 16 |

The concentration of BSO was 1 mM for all cell lines except HT 144, where the concentration was 0.25 mM. Cells were seeded in the recommended growth medium at a density of $1.5 \times 10^4$ cell/cm$^2$ into 2 cm$^2$ wells. Drugs were added simultaneously 4 hours after seeding, and incubation was continued for 48 hours at 37° C. in a 5% $CO_2$ atmosphere. For assessment of drug effects cells were detached by trypsinization and counted in a hemacytometer.

Cell lines Nos. 1–4 were obtained from Dr. C. Benz, University of California, San Francisco. MDA 468 and MCF-7 human mammary cancer lines, MCF-7-B-ADR drug-resistant mammary cancer line, Du 145 drug-resistant human prostate cancer line, HT 144 human melanoma cell line, Hep-G2 human hepatocellular carcinoma line, and PC-12 rat pheochromocytoma line were obtained from the University of California Cell Culture Facility. Each value in Table 3 is an average of two parallels, each of which did not deviate from the average by more than±15%.

As summarized in Table 3 seven types of human cancer cells cultured as monolayers and five types of leukemia cells grown as suspension cultures responded to BSO by a dramatic increase in the apoptosis-inducing potency of $INO_2BA$. Notable are the MCF-7-B-ADR adriamycin-resistant human mammary cancer cell line and the Du-145 drug-resistant prostatic cancer cell line. That reduction of the C-nitro precursor to the active C-nitroso compound is essential for induction of apoptosis is evident from the large synergistic effect of BSO, which by diminishing cellular levels of GSH decreases the rate at which GSH chemically reduces, and thus inactivates, the active C-nitroso compounds generated in vivo.

X. Non-Toxicity of $INO_2BA$ and BSO

Twelve hamsters of both sexes were injected intraperitoneally with 200 mg/kg $INO_2BA$ daily for 14 days without toxic effects.

The non-toxicity of BSO has been reported in the literature. See, e.g., Liebman et al., *Cancer Res.* 53:2066–2070 (1993); Yao et al., *Cancer Res.* 53:3662–3666 (1993); Terradez et al., *Biochem J.* 292:477–483 (1993); and Polhuijs et al., *Biochem J.* 285:401–404 (1992).

XI. Zinc loss from Treatment of HIV-1 Virions with NOBA

Experiments were performed to determine if NOBA is capable of ejecting zinc from intact virions. HIV-1 (MN strain) was produced, purified and concentrated as described in Bess et al., *J. Virol.* 66:840–847 (1992). The concentrated virus was diluted to 60 times that of culture fluid in TNE buffer (0.01M Tris-HCl, 0.1M NaCl, 1 mM EDTA, pH 7.2) and incubated with 3000 or 6000 $\mu$M NOBA at 37° C. The virus was then pelleted and washed with TNE buffer to remove weakly bound zinc. The quantity of zinc in the resulting viral pellets was determined as described in Bess et al., *J. Virol.* 66:840–847 (1992). No significant loss of viral proteins in the pellet was detected by p24 and gp120 competition radioimmunoassays and coumassie-stained sodium dodecyl sulfate polyacrylamide gel electrophoresis.

The data in Table 4 demonstrate that treatment of concentrated suspensions of HIV-1 (60× with respect to culture solution) with NOBA results in losses of 50–83% of the viral zinc and complete loss of infectivity. Since edge x-ray absorption fine structure spectroscopy has shown that the majority of the zinc in intact retroviruses is coordinated by the CCHC ligands, Summers et al., *Protein Science* 1:563–574 (1992) and Chuang et al., *Proc. Natl. Acad. Sci.* 89: (1992), the ejection of zinc from virions by NOBA is directly attributable to a destablization of the nucleocapsid CCHC zinc fingers.

TABLE 4

| NOBA ($\mu$M)[a] | Incubation time (hr) | Zinc, Control Sample ($\mu$g/ml) | Zinc, NOBA-Treated Sample ($\mu$g/ml) | Zinc Loss (%) |
|---|---|---|---|---|
| 3,000 | 2 | 0.21 | 0.11 | 52 |
| 6,000 | 4 | 0.24 | 0.04 | 83 |

[a]concentrations correspond to molar NOBA:zinc finger ratios of ca. 350:1 (3,000 $\mu$M) and 700:1 (6,000 $\mu$M)

XII. In Vitro Anti-Retroviral Testing of 6-NOBP and NOBA

Figure 7A:
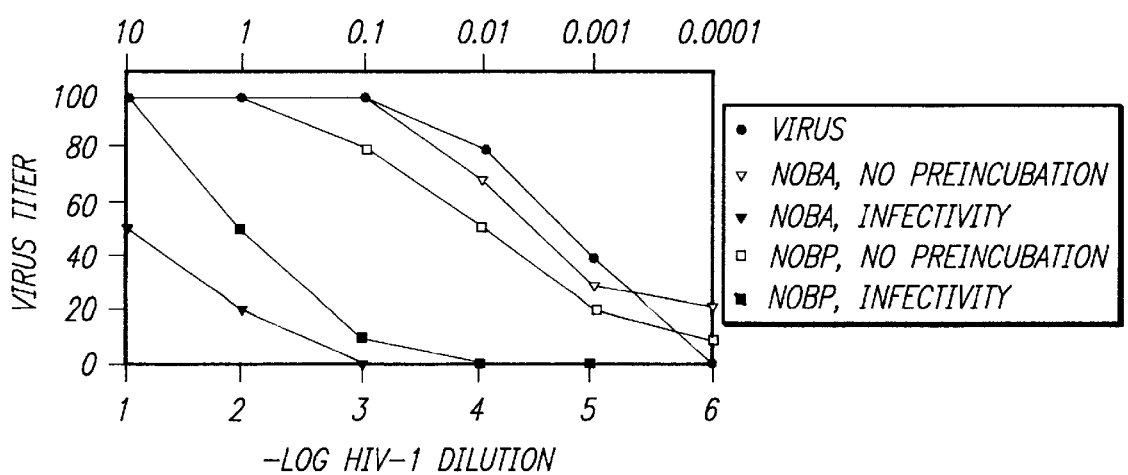
FIG. 7A shows the HIV-1 inactivation assay using NOBA and NOBP (6-nitroso-1,2-benzopyrone). The HIV-1 stock (HIV-1 100,000 TCID$_{50}$ was treated for 30 min. with 100 μM NOBP at 22° C., the mixture was serial 10-fold diluted and inoculated into PBL cultures. After 9 days the culture supernatants were harvested and the frequency of infected cultures was measured by immunoassay. The percent positive of cultures was then plotted as a function of the virus input titer. The relative amount of infectious virus available to cause 50% infected cultures was decreased by 4 log units with NOBA.
Figure 7B:
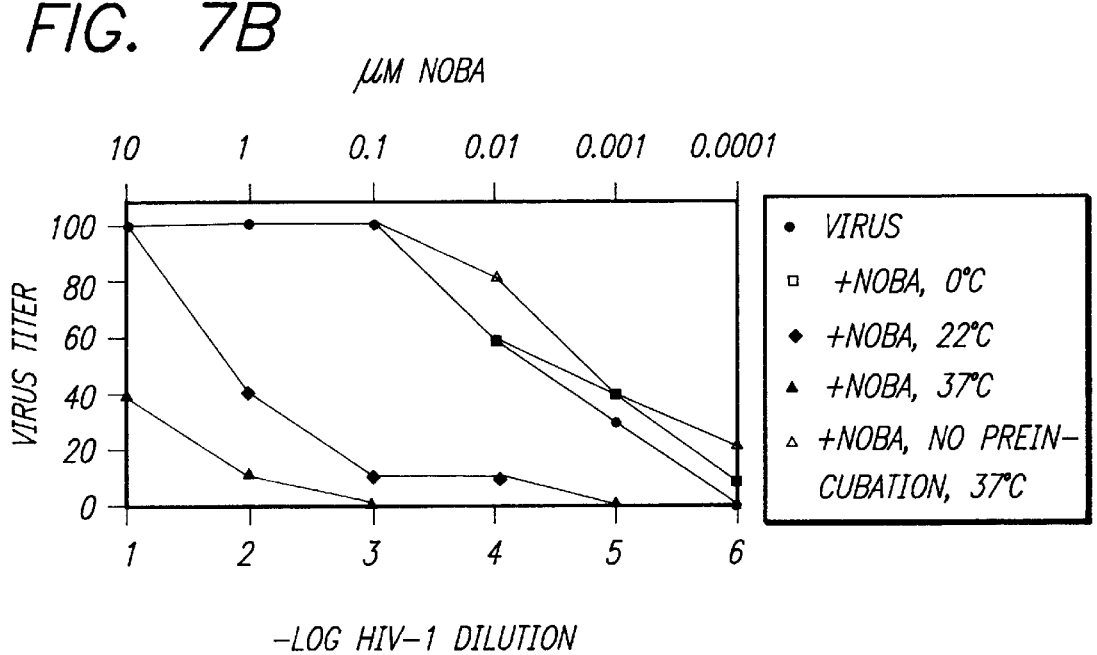
FIG. 7B shows an HIV-1 inactivation assay with NOBA at different temperatures. The assay was performed as described in FIG. 7A except that the 30 min. preincubation of virus with NOBA was carried out at 0°, 22° or 37° C.
Figure 7C:
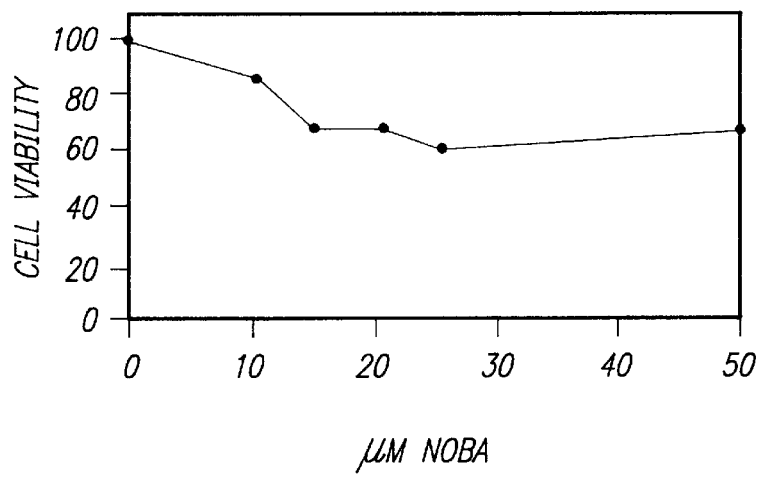
FIG. 7C shows the dose-response effect of NOBA on the viability of PHA-PBL. Cells ($10^6$/ml) were treated with increasing doses of NOBA for 24 hours in the presence of MTT indicator and the relative absorbance at 550 nm reflects the metabolic activity of the cells. The level of product formation in the absence of NOBA was considered to be 100% and all experimental values were normalized to that control value.

Both 6-NOBP and NOBA were tested on viral growth of HIV-1 (LAV strain) in phytohemagglutinin-stimulated human peripheral lymphocytes (PBL). An HIV-1 stock having an infectivity titer of 100,000 $TCID_{50}$ was incubated for 30 min. at 22° C. with either of the drugs. Control HIV samples, containing no drugs, were incubated in the same manner. Following successive serial dilutions of 10-fold that resulted in HIV-1 titers as given in the lower abscissa of FIG. 7 (A,B), viral growth was initiated by adding the HIV-1 dilutions to PBL and allowing an incubation period of 9 days. At the end of this incubation cultures were assayed for productive infection by an immunoassay for HIV-1 antigens and by reverse transcriptase as described in McDougal et al., *J. Immunol. Methods* 76:171–183 (1985). Virus titers were expressed as percentile values (percent infected cultures) compared to the controls, containing HIV dilutions which were not preincubated with the C-nitroso drugs. In a separate series of experiments, HIV-1 dilutions and C-nitroso drugs (see upper abscissa) were not preincubated but were added simultaneously to lymphocytes in exactly the same concentrations as described previously (i.e., following preincubation) and viral growth monitored 9 days later. As illustrated in FIG. 8, the inhibition of HIV-1 propagation was profound when C-nitroso drugs were preincubated with HIV-1.

XIII. Anti-Viral Activity of C-Nitro- and C-Nitroso-Containing Compounds

TABLE 5

HIV Activity in Human Lymphocyte of pADPRT Ligands Calculated Infections Titer of Virus After Treatment

| Treatment | Dose (μM) | TCID$_{50}$ | Decrease | Inhibition |
|---|---|---|---|---|
| No Drug | No Drug | 177,828 | – | – |
| NO$_2$BP | 500 | 85,114 | 0.32 | 52.14 |
| NOBP | 100 | 102 | 3.24 | 99.94 |
| NOBA | 100 | 11 | 4.20 | >99.99 |

6-Nitro-1,2-benzopyrone ("NO$_2$BP"), an in vivo pro-drug of NOBP inhibited HIV-1 activity in human lymphocytes 52% by reduction to the active nitroso form in vivo. Since the nitro compound is more stable and soluble than the active nitroso compound, which in the solid form is a poorly soluble dimeric species, supplying the nitro pro-drug provides a constant in vivo supply of the active nitroso compound for inhibiting viral growth and reproduction.

XIV. Synergistic Anti-Viral Effects of BSO and INO$_2$BA

CEM x174 cells (3×10$^5$/ml) were infected with 3.75 TCID$_{50}$/ml (50% tissue culture infectious dosage per ml of cell suspension) stock solution of SIVmac239 or virus isolates from SIVmac239-infected rhesus macaques on day 0. Uniform infection of cells was ensured by the infection of one cell population only per virus preparation. Three days post-infection, the cells were distributed (500 μl/well) into individual wells of a 24-well plate. Fresh medium containing INO$_2$BA concentrations ranging from 0 to 300 μM and/or BSO concentrations ranging from 0 to 0.25 mM were added to establish final 1-ml reaction volumes, and the cultures were further incubated for 4 days. The wells were then replenished with fresh CEM x174 cells (3×10$^5$/ml), INO$_2$BA and/or BSO were re-added at the same concentrations as in the original incubates, and incubation was continued for an additional 3 days. This procedure intends to mimic conditions of in vivo chemotherapy. Cell viability and virus titers in the supernatant were determined on day 10 (3 days after the addition of new cells) by the tetrazolium (MTT) method of Hansen et al., *J. Immunol. Methods* 119:208–210 (1982) and by the SIV p27 and reverse transcriptase (RT) assays described by Chuang et al., *FEBS Lett.* 326:140–144 (1993), respectively.

The viability of infected and uninfected cell cultures was determined by the method of Hansen et al., *J. Immunol. Methods* 119:208–210 (1982). Briefly, MTT was dissolved in sterile phosphate buffered saline (PBS) at a concentration of 5 mg/ml and 20 μl of MTT solution was added into each microtiter well containing 100 μl of cell culture. After 2 hr incubation at 37° C., 100 μl of solubilizing solution was added. Following overnight incubation at 37° C., optical absorbance were measured at 570 nm using a microtiter plate reader (Molecular Devices Corp., Sunnyvale, Calif.).

To evaluate the activity of SIV reverse transcriptase, 10 μl of infected cell supernatant was added to a reaction mixture containing 50 mM Tris-HCl (pH 8.0), 5 mM MgCl$_2$, 10 mM dithiothreitol, 20 mM KCl, and 1% Triton X-100 in a total volume of 50 μl. Poly(rA):oligo (dT)$_{12-18}$ was present at 100 μg/ml and 2.4 μM [$^3$H]TTP was used. The reaction mixtures were incubated at 37° C. for 1 hr and the TCA-precipitable radioactivity was filtered onto nitrocellulose filters which were then washed, dried and counted.

SIVmac p27 core antigen levels were determined by an enzyme immunoassay provided by Coulter Corp. (Hialeah, Fla.). The assay was performed according to the manufacturer's specifications.

Figure 4A:
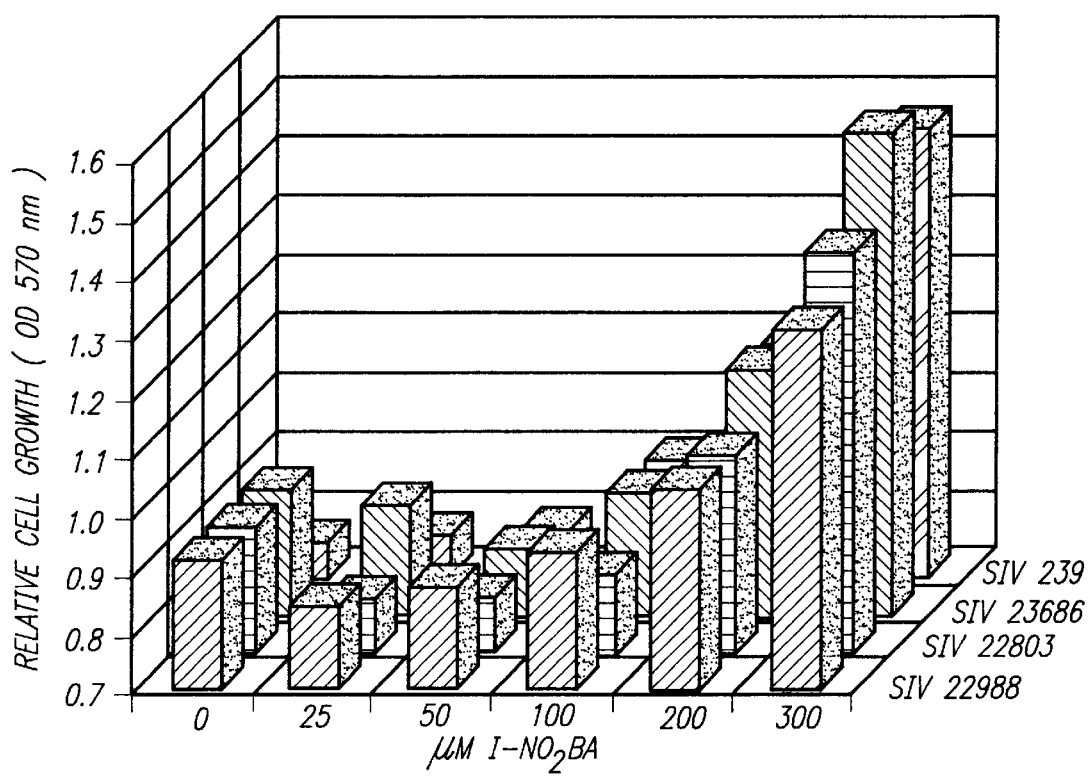
FIG. 4 shows the effects of INO$_2$BA alone (FIG. 4A) and in combination (FIG. 4B) with various concentrations of BSO on the viability of CEM ×174 cells infected with SIV as determined by the tetrazolium assay. In both (A) and (B) the ordinate represents cell viability on day 10 of the assay and the abscissa represents the concentration of INO$_2$BA in the absence of BSO (FIG. 4A), and in the presence of BSO (FIG. 4B).
Figure 4B:
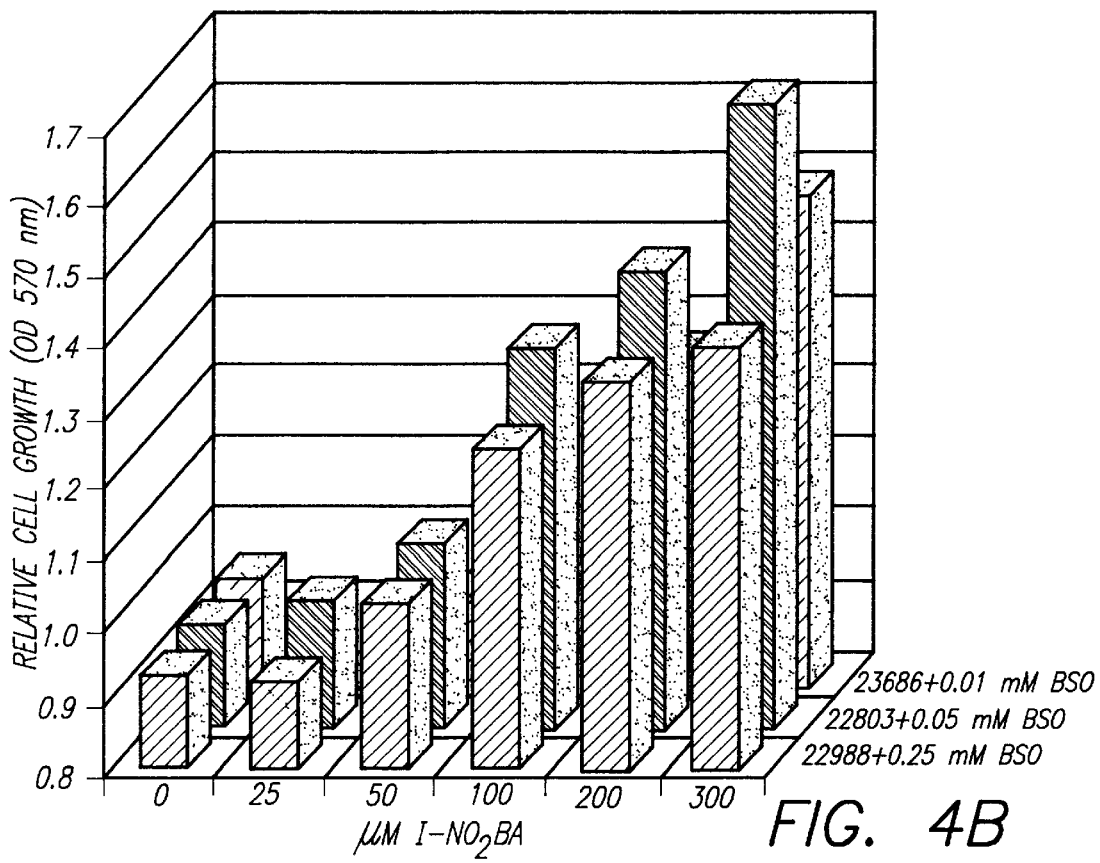

The results of these experiments are shown in FIGS. 4 and 5. Just like the inhibition of syncytia formation by the drug, apparent cell viability (tested by the MTT assay) was protected by INO$_2$BA, indirectly indicating a depression of viral replication. Four SIV strains behaved essentially in a similar manner, and INO$_2$BA increased cell viability proportional to decreasing viral replication, with BSO supporting this effect. See FIGS. 4A and 4B.

Figures 5A, 5B:
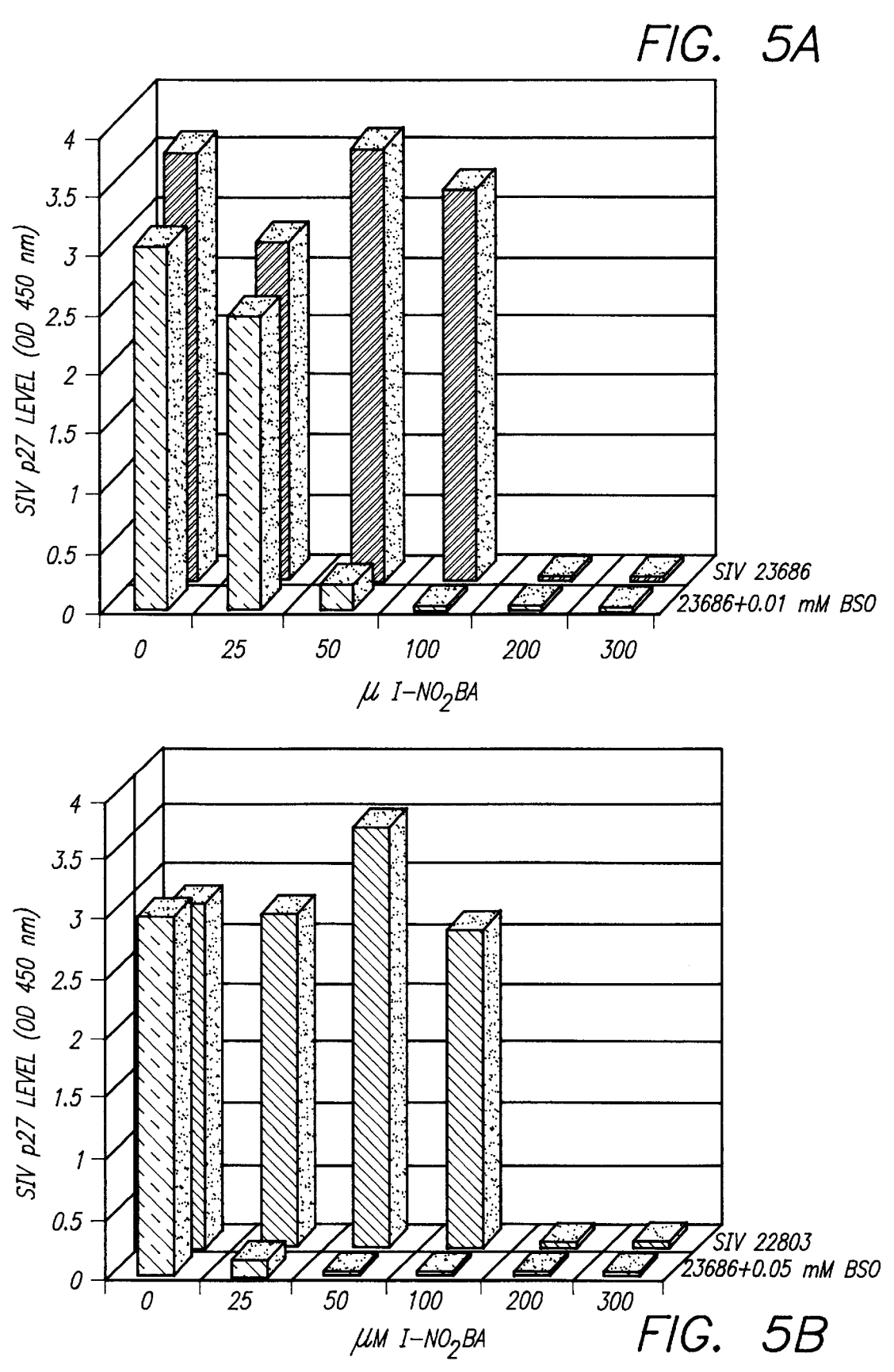
Figure 5C:
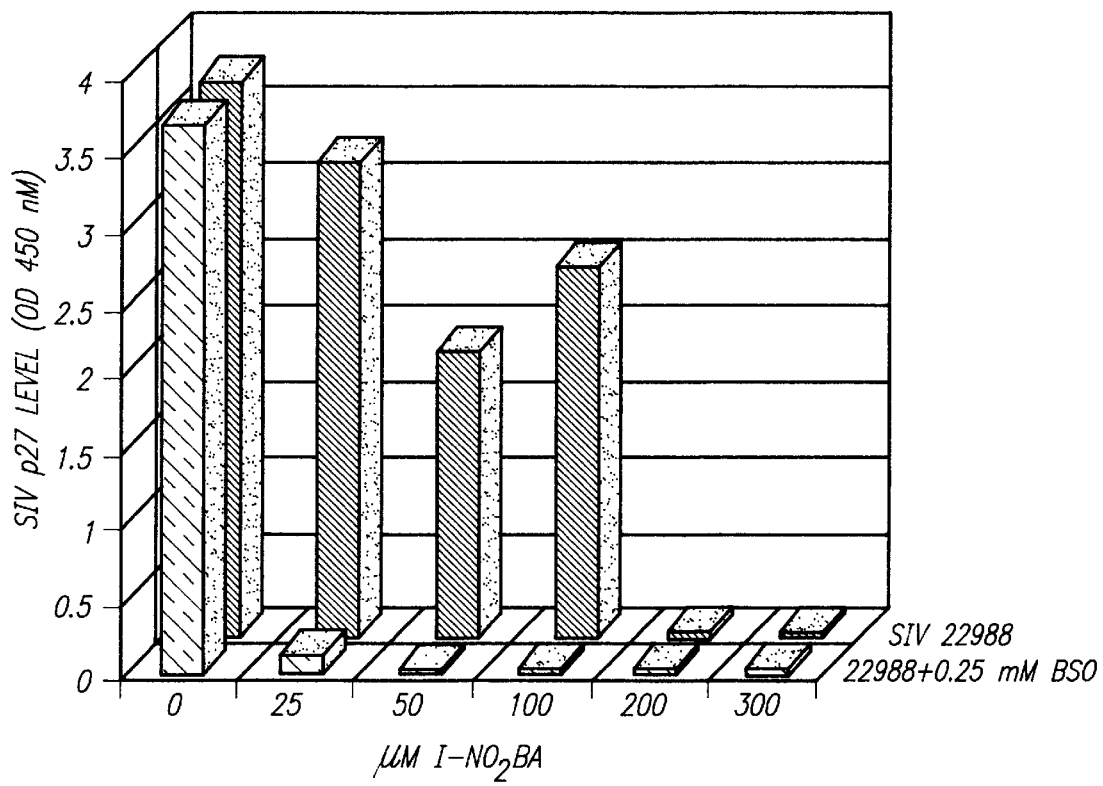
FIG. 5 shows the effect of INO$_2$BA alone and in combination with BSO on SIV replication. Infected cell cultures described in FIG. 4 were used for determination of supernatant virus titers by SIV p27 core antigen assay as described in Example XIV. The ordinate represents p27 ELISA performed on day 10 of the assay and the abscissa represents the concentration of INO$_2$BA alone (rear rows in panels A, B and C) and in combination with BSO (front rows in panels A, B and C). Panel D shows that various concentrations of BSO alone have no effect on SIV replication.
Figure 5D:
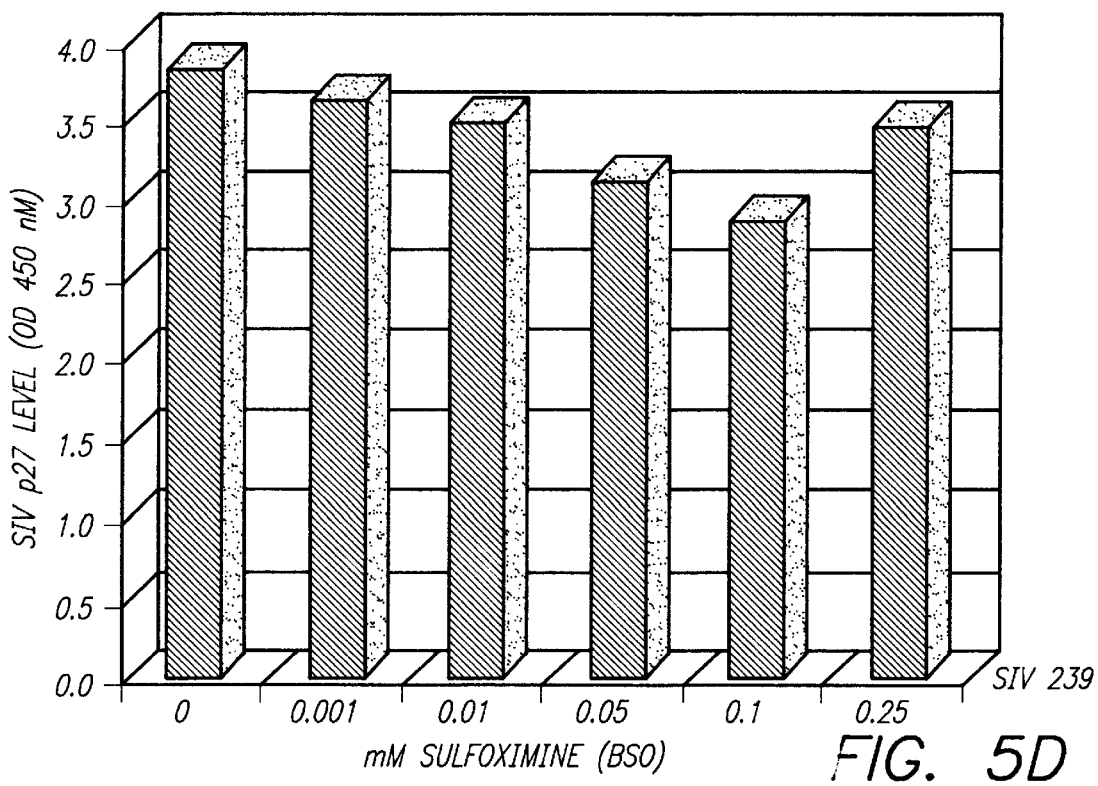
Figure 6:
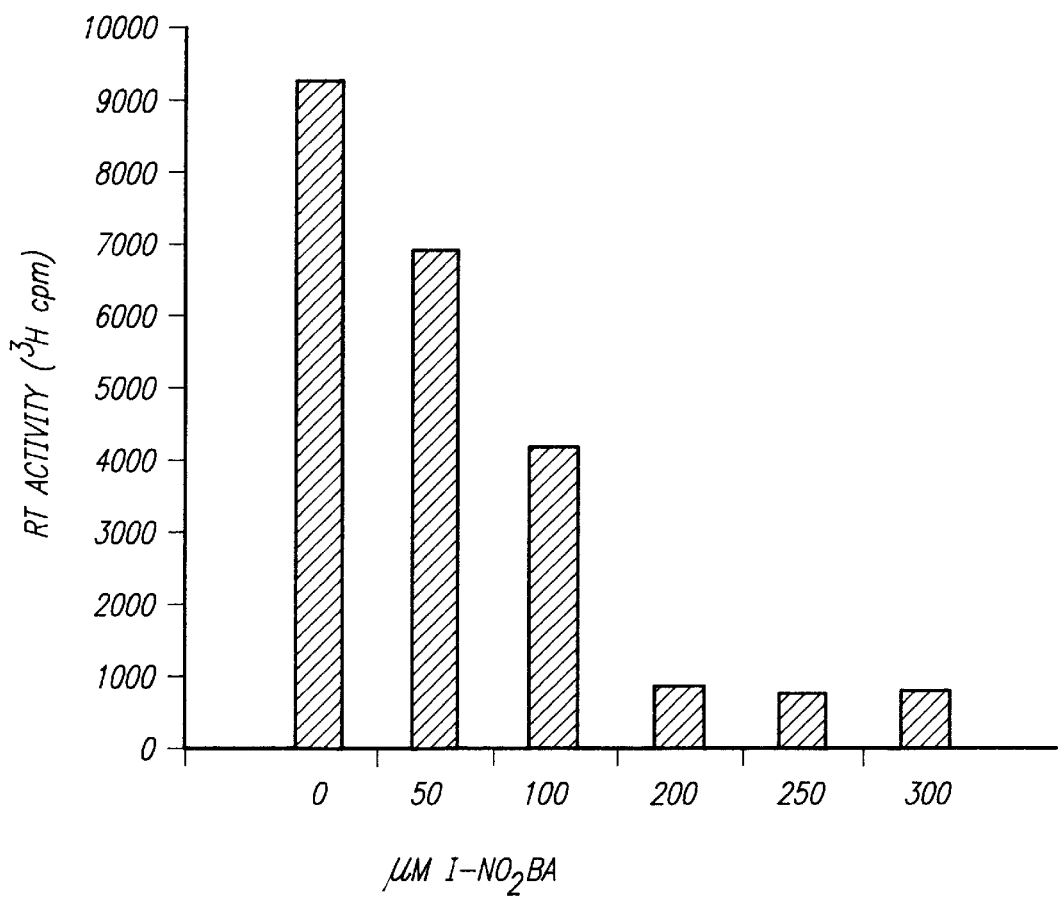
FIG. 6 shows the effect of INO$_2$BA on SIVmac replication in CEM ×174 cells pre-infected with virus prior to treatment with INO$_2$BA, as determined by the reverse transcription assay.

A more direct anti-SIV activity is illustrated in FIGS. 5A, 5B and 5C, where a decrease to almost complete inhibition of SIV p27 formation is apparent as a function of INO$_2$BA concentration. By itself, BSO had no effect on p27 formation (FIG. 5D). With a combination of BSO and varying concentrations of INO$_2$BA (10, 50 and 250 μM), in various SIV strains, p27 formation was markedly depressed, an effect that roughly correlated with the inhibition of syncytia formation. As an independent assay of viral replication, reverse transcriptase activity of SIV-infected CEM x174 cells was greatly depressed by INO$_2$BA (FIG. 6).

Just as in tumor cells where a slow reduction of the prodrug INO$_2$BA to the bioactive INOBA produces cell killing, an anti-SIV effect of the prodrug is apparent in the CEM x174 cell line. This cell line, requiring no stimulation by phytohemagglutinin for viral growth, is a fusion product of human B cell line 721.174 and T cell line CEM. Slater et al., *Immunogenics* 21:235–246 (1985). As is the case with many established immortal cell lines it does not exhibit a normal phenotype since it is immortal. If the assumption that undifferentiated cells have an impaired NADPH oxidase system, Trudel et al., *Biochem J.* 278:611–619 (1964), is valid for CEM x174 cells, this defect also predisposes these cells to reduce INO$_2$BA to the active nitroso species, contrary to the behavior of normal cells containing intact NADPH oxidase. However, present results indicate that replication of HIV in intact human macrophages, which presumably have no defective NADPH oxidase, is readily inhibited by the prodrug INO$_2$BA. Kun et al., Abstract 422A, *Tenth International Conference on AIDS*, Yokohama, Japan (1994). This poses the question whether retroviral infection by itself is capable of interfering with NAPDH oxidase. If so, this condition may promote the selectivity of INO$_2$BA towards HIV or SIV infected cells in vivo. The highly effective synergistic action of BSO with INO$_2$BA strongly supports the contention that the nitroso species (INOBA) exerts its direct action on retroviral CCHC zinc fingers, as reported earlier, Rice et al., *Nature* 361:473–475 (1993), because depression of cellular GSH by BSO produces a higher, and thus more effective, concentration of the nitroso drug in the cell.

XV. The Effect of INO$_2$BA on SIVmac Replication in CEM x174 Cells Pre-Infected with Virus Before Treatment with INO$_2$BA The effect of INO$_2$BA on SIVmac replication in CEM x174 cells that were pre-infected with virus for one day prior to treatment with INO$_2$BA are shown in FIG. 6. The cell culture and SIV reverse transcription assay were performed as described in Example XIV.

This experiment clearly indicates that INO$_2$BA is effective even when incubated with cells that have been infected with virus prior to INO$_2$BA addition, whereas NOBA requires pre-incubation with cells prior to viral infection.

XVI. Synergistic Effect of INO$_2$BA and BSO on AZT-Resistant SIV Propagation

The synergistic effect of INO$_2$BA in combination with BSO on AZT-resistant SIV propagation is shown in Table 6.

TABLE 6

The Synergistic effect of INO$_2$BA and BSO on AZT-resistant SIV propagation

| Virus | INO$_2$BA ($\mu$M) | BSO (mM) | Syncytia |
|---|---|---|---|
| SIV 23686 (AZT-resistant) | 0 | 0 | +++ |
| | 25 | 0 | ++ |
| | 50 | 0 | ++ |
| | 100 | 0 | ++ |
| | 200 | 0 | + |
| | 300 | 0 | − |
| | 0 | 0.01 | +++ |
| | 25 | 0.01 | + |
| | 50 | 0.01 | + |
| | 100 | 0.01 | − |
| | 200 | 0.01 | − |
| | 300 | 0.01 | − |
| SIV 22803 (AZT-resistant) | 0 | 0 | +++ |
| | 25 | 0 | ++ |
| | 50 | 0 | ++ |
| | 100 | 0 | ++ |
| | 200 | 0 | − |
| | 300 | 0 | − |
| | 0 | 0.05 | ++++ |
| | 25 | 0.05 | − |
| | 50 | 0.05 | − |
| | 100 | 0.05 | − |
| | 200 | 0.05 | − |
| | 300 | 0.05 | − |

CEM × 174 (3 × 10$^5$/ml) were infected with equal doses of SIVmac239 or virus isolates from SIVmac239-infected rhesus macaques (MMU 23686, 22803). Three days post-infection, INO$_2$BA concentrations ranging from 0 to 300 $\mu$M with or without BSO were added, and incubated for an additional 3 days. Cell cultures were then examined for syncytia formation. The number of syncytia in cell cultures was counted in arbitration fields under 40× magnification and scored as follows: over 30 (++++), 20–30 (+++), 10–20 (++), 1–9 (+), and 0 (−).

The infection of CEM ×174 cells with SIVmac virus resuls in synctia formation and eventual cell death by lysis. Chunang et al., *Biochem Biophys. Res. Commun.* 195:1165–1173 (1993). In 4 days an AZT-resistant SIV strain (SIV-23686) induced between 20–30 syncytia per visual field. However increasing concentrations of INO$_2$BA (from 25 to 300 $\mu$M) effectively abolished cell fusion above 200 $\mu$M drug concentration. A second AZT-resistant strain (SIV-22803) produced over 30 syncytia and required higher than 100 $\mu$M INO$_2$BA to abrogate cell fusion. When BSO was added simultaneously with the drug, the inhibitory effect on syncytia formation was greatly enhanced, and as little as 0.01 mM BSO (in SIV-23686) lowered the inhibitory concentration of INO$_2$BA to 50 $\mu$M, whereas 0.05 mM BSO decreased the syncytia-blocking concentration INO$_2$BA to 25 $\mu$M (in SIV-22803). Differences between strains may be related to intracellular GSH, which is probably affected differently by the two viral strains.

Figure 10:
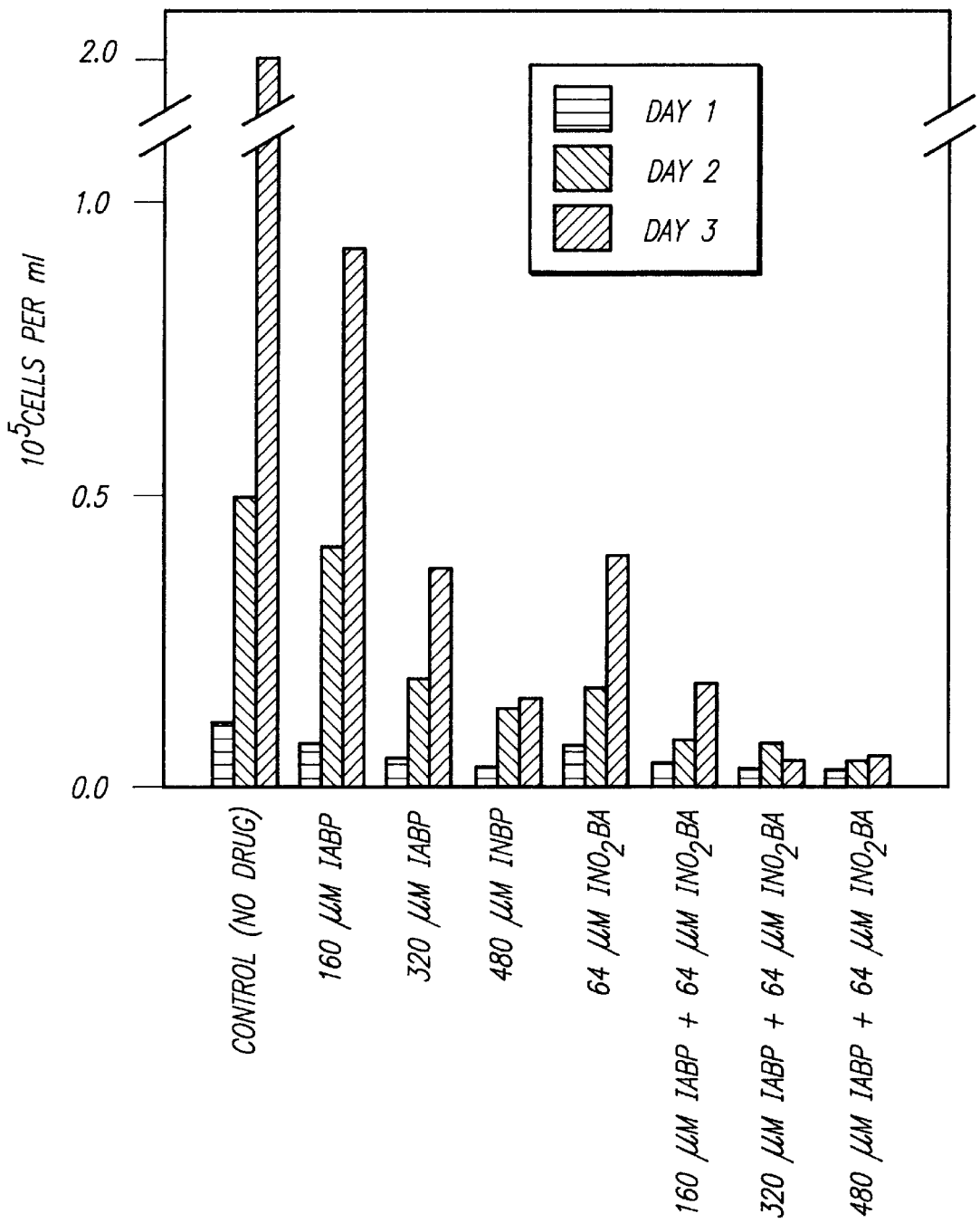
FIG. 10 shows the synergistic effect of IABP and $INO_2BA$, each alone and in combination, on the growth of L 1210 cancer cells.

XVII. Synergistic Cytotoxic Effect of IABP in Combination with INO$_2$BA in L 1210 Cells The synergistic effect of IABP in combination with INO$_2$BA in L 1210 cells is shown in FIG. 10. As can be seen in the Figure, 160 $\mu$M, 320 $\mu$M and 480 $\mu$M IABP decreased L 1210 cell proliferation by approximately 55%, 80% and 93%, respectively, over a three day growth period. 64 $\mu$M INO$_2$BA decreased L 1210 cell proliferation by approximately 80% over a three day growth period. 64 $\mu$M in combination with 160 $\mu$M, 320 $\mu$M and 480 $\mu$M IABP, respectively, decreased L 1210 proliferation by about 90%, 98% and 97%, respectively, demonstrating the synergistic cytotoxic effect of IABP in combination with INO$_2$BA.

XVIII. Inhibitory Effect of IABP on SIVmac239 Replication

The effect of IABP on the infection cycle of SIV was determined. CEM ×174 cells (3×10$^5$/ml) were infected with SIVmac239 on day 0 and incubated for 3 days (37 20 C., 5% CO$_2$) before treatment with IABP (0–0.5 mM). The cultures were incubated for an additional 4 days before being replenished with fresh CEM ×174 cells (3×10$^5$/ml) and IABP. On day 10 the levels of free virus in the supernatants of the cultures were assessed using the SIV p27 core antigen assay (Coulter Copr.) The absorbance was measured at 450 nm.

The results are shown in FIG. 8. IABP has no toxic effect on cells, Cole et al., *Biochem Biophys. Res. Commun.* 180:504–514 (1991), and depresses p27 levels proportional to its concentration.

XIX. Synergistic Anti-Retroviral Effect of IABP in Combination with INO$_2$BA

Figure 9A:
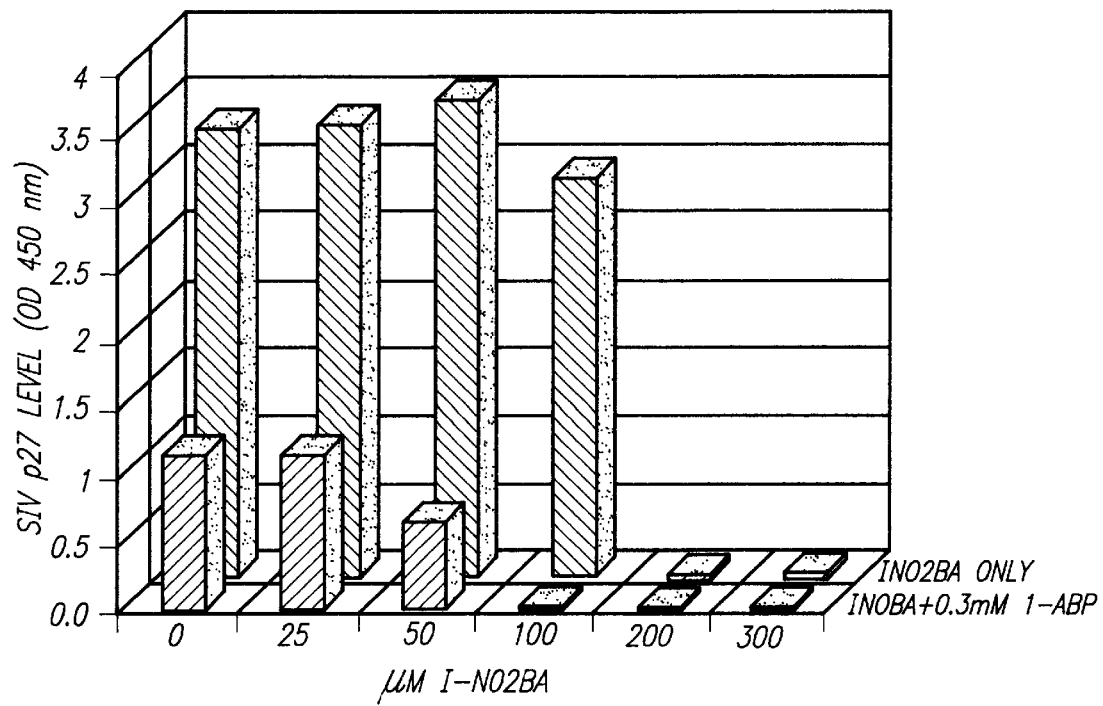
FIG. 9A shows the synergistic effect of IABP in combination with $INO_2BA$ on SIVmac239 replication. Cells ($1\times10^6$/ml) were infected with SIVmac239 on day 0 and incubated for 3 days (37° C., 5% $CO_2$) before treatment with $INO_2BA$ (0–300 μM) (rear columns) or with $INO_2BA$ and IABP (0.3 mM) (front columns). The cultures were incubated for an additional 4 days before being replenished with fresh CEM ×174 cells ($3\times10^5$/ml) and drug(s). On day 10 the levels of free virus in the supernatants were assessed using the SIV p27 core antigen assay, with absorbance measured at 450 nm.

The synergistic effect of IABP in combination with INO$_2$BA on SIVmac239 replication was demonstrated. CEM ×174 cells (1×10$^6$/ml) were infected with SIVmac239 on day 0 and incubated for 3 days (37° C., 5% CO$_2$) before treatment with INO$_2$BA (0–300 $\mu$M) (rear columns) or with INO$_2$BA and IABP (0.3 mM) (front columns). The cultures were incubated for an additional 4 days before being replenished with fresh CEM ×174 cells (3×10$^5$/ml) and drug(s). On day 10 the levels of free virus in the supernatants of the cultures were assessed using the SIV p27 core antigen assay (Coulter Copr.), with absorbance measured at 450 nm. The results are shown in FIG. 9A.

The synergistic effect of IABP in combination with INO$_2$BA on the viability of SIVmac239-infected CEM ×174 cells was also demonstrated. The procedure was the same as that described in the preceding paragraph. The cell viability of the cultures was measured by the MTT assay on day 10 of the experiment. The results are shown in FIG. 9B. The effect of INO$_2$BA alone is shown in the front columns, and the drug combination in the rear columns.

A more than additive anti-SIV action of 0.3 mM IABP and varying concentrations of INO$_2$BA, as assayed by the inhibition of p27 formation in SIV-infected CEM ×174 cells, was observed. This drug combination also supported cell growth more than additively in the presence of SIV.

XX. Non-Toxicity of IABP

The non-toxicity of IABP is demonstrated in Cole et al., *Biochem Biophys. Res. Commun.* 180:504–514 (1991).

EQUIVALENTS

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A synergistic composition comprising one or a plurality of pADPRT CCHC-oxidizing ligands in combination with one or a plurality of non-covalent pADPRT-inhibitory ligands wherein the pADPRT CCHC-oxidizing ligands are selected from the group consisting of:

a compound having the formula:

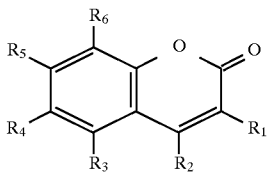

wherein $R_1$, $R_2$, $R_3$, $R_4$, $R_5$ and $R_6$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen and wherein at least one of the six $R_1$, $R_2$, $R_3$, $R_4$, $R_5$ and $R_6$ substituents is nitroso or nitro;

a compound having the formula:

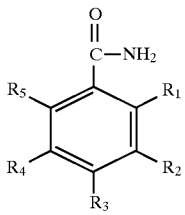

wherein $R_1$, $R_2$, $R_3$, $R_4$ and $R_5$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are hydrogen and wherein at least one of the six $R_1$, $R_2$, $R_3$, $R_4$, $R_5$ and $R_6$ substituents is nitroso or nitro;

and a compound having the formula:

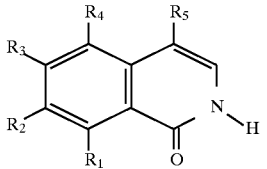

wherein $R_1$, $R_2$, $R_3$, $R_4$ and $R_5$ are, independent of one another, selected from the group consisting of hydrogen, hydroxy, nitroso, nitro, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least two of the five $R_1$, $R_2$, $R_3$, $R_4$ and $R_5$ substituents are hydrogen and wherein at least one of the five $R_1$, $R_2$, $R_3$, $R_4$, and $R_5$ substituents is nitroso or nitro;

and wherein the non-covalent pADPRT-inhibitory ligands are selected from the group consisting of:

a compound having the formula

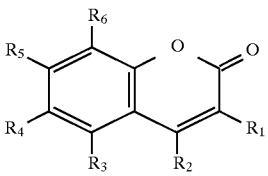

wherein $R_1$, $R_2$, $R_3$, $R_4$, $R_5$ and $R_6$ are, independent of one another, selected from the group consisting of hydrogen, hydroxy, amino, iodo, ($C_1$–$C_6$) alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen; and a compound having the formula:

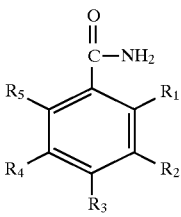

wherein $R_1$, $R_2$, $R_3$, $R_4$, $R_5$ and $R_6$ are, independent of one another, selected from the group consisting of hydrogen, hydroxy, amino, iodo, alkyl, ($C_1$–$C_6$) alkoxy, ($C_3$–$C_7$) cycloalkyl, and phenyl and pharmaceutically acceptable salts thereof, wherein at least three of the six $R_1$, $R_2$, $R_3$, $R_4$, $R_5$ and $R_6$ substituents are hydrogen.

2. The composition of claim 1 wherein said non-covalent pADPRT-inhibitory ligands are selected from the group consisting of 6-amino-1,2-benzopyrone and 5-iodo-6-amino-1,2-benzopyrone.

3. A pharmaceutical formulation comprising a composition according to claim 1 and a pharmaceutical excipient.

4. A method of inducing apoptosis in a tumor cell comprising the step of administering to a cell culture or mammalian host having said tumor cell a composition according to claim 1.

5. A method for the treatment of cancer comprising the step of administering to a mammal an effective amount of a composition according to claim 1.

6. The synergistic composition of claim 1, wherein said pADPRT CCHC-oxidizing ligand comprises 4-iodo-3-nitrobenzamide and wherein said non-covalent pADPRT-inhibitory ligand comprises 5-iodo-6-amino-1,2-benzopyrone.

* * * * *